(12) United States Patent
Blatter et al.

(10) Patent No.: US 7,124,570 B2
(45) Date of Patent: Oct. 24, 2006

(54) APPARATUS AND METHODS FOR FLUID OCCLUSION OF AN ACCESS TUBE ANASTOMOSED TO AN ANATOMICAL VESSEL

(75) Inventors: Duane D. Blatter, Salt Lake City, UT (US); Troy J. Orr, Draper, UT (US); Michael C. Barrus, Centerville, UT (US)

(73) Assignee: Integrated Vascular Interventional Technologies, L.C., Salt Lake City, UT (US)

( * ) Notice: Subject to any disclaimer, the term of this patent is extended or adjusted under 35 U.S.C. 154(b) by 373 days.

(21) Appl. No.: 10/624,711

(22) Filed: Jul. 21, 2003

(65) Prior Publication Data

US 2004/0147867 A1    Jul. 29, 2004

Related U.S. Application Data

(63) Continuation-in-part of application No. 10/351,172, filed on Jan. 23, 2003.

(51) Int. Cl.
 *A61M 37/00* (2006.01)
 *A61M 5/00* (2006.01)
 *A61M 1/00* (2006.01)

(52) U.S. Cl. ............... 60/6.16; 604/4.01; 604/5.01; 604/7; 604/28; 604/264

(58) Field of Classification Search ........... 604/4.01, 604/5.01, 5.04, 6.05, 6.06, 6.1, 7–10, 28, 604/6.16, 96.01, 101.04, 103.07, 508, 509, 604/30, 27; 623/1.25, 1.36; 210/600, 645, 210/646; 128/898; 606/153
See application file for complete search history.

(56) References Cited

U.S. PATENT DOCUMENTS

| | | | |
|---|---|---|---|
| 3,392,722 A | 7/1968 | Jorgensen | |
| 3,395,710 A | 8/1968 | Stratton et al. | |
| 3,713,441 A | 1/1973 | Thomsd | |
| 3,826,257 A | 7/1974 | Buselmeier | |
| 3,853,126 A | 12/1974 | Schulte | |
| 3,991,756 A | 11/1976 | Snyder | |
| 4,122,858 A | 10/1978 | Schiff | |
| 4,301,797 A | 11/1981 | Pollack | |
| 4,318,401 A | 3/1982 | Zimmerman | |
| 4,366,810 A | 1/1983 | Slanetz, Jr. | |
| 4,370,983 A | 2/1983 | Lichtenstein | |
| 4,421,507 A * | 12/1983 | Bokros | ............ 604/539 |
| 4,623,348 A | 11/1986 | Feit | |
| 4,655,771 A | 4/1987 | Wallsten | |
| 4,819,637 A | 4/1989 | Dormandy, Jr. et al. | |

(Continued)

OTHER PUBLICATIONS

Lycos, Your Personal Internet Guide, APHERESIS, located at http://infoplease.lycos.com/ipd/A0321273.html, 1 pg., printed May 22, 2002.

(Continued)

*Primary Examiner*—Patricia Bianco
*Assistant Examiner*—Leslie Deak
(74) *Attorney, Agent, or Firm*—Stoel Rives LLP

(57) ABSTRACT

The invention provides a vascular access system and methods for facilitating long-term, repeated access to any of a patient's vascular systems. This is provided by an access tube apparatus adapted for anastomosis to an anatomical vessel. The access tube is occluded with an fluid occluder that fits within the conduit of the access tube in between treatments or when vascular access is otherwise not needed. When such access is desired, the fluid occluder is withdrawn from the access tube and the body fluid is accessed through the access tube.

41 Claims, 17 Drawing Sheets

U.S. PATENT DOCUMENTS

| | | | | |
|---|---|---|---|---|
| 4,822,341 | A | * | 4/1989 | Colone ..................... 604/175 |
| 4,846,186 | A | | 7/1989 | Box et al. |
| 5,092,841 | A | | 3/1992 | Spears |
| 5,102,402 | A | | 4/1992 | Dror et al. |
| 5,290,306 | A | | 3/1994 | Trotta et al. |
| 5,304,220 | A | | 4/1994 | Maginot |
| 5,411,475 | A | | 5/1995 | Atala et al. |
| 5,417,657 | A | | 5/1995 | Hauer |
| 5,443,497 | A | | 8/1995 | Venbrux |
| 5,456,712 | A | | 10/1995 | Maginot |
| 5,458,568 | A | | 10/1995 | Racchini et al. |
| 5,478,320 | A | | 12/1995 | Trotta |
| 5,613,979 | A | | 3/1997 | Trotta et al. |
| 5,616,114 | A | | 4/1997 | Thornton et al. |
| 5,617,878 | A | | 4/1997 | Taheri |
| 5,620,649 | A | | 4/1997 | Trotta |
| 5,634,936 | A | | 6/1997 | Linden et al. |
| 5,662,580 | A | | 9/1997 | Bradshaw et al. |
| 5,662,700 | A | | 9/1997 | Lazarus |
| 5,693,088 | A | | 12/1997 | Lazarus |
| 5,695,504 | A | | 12/1997 | Gifford, III et al. |
| 5,702,412 | A | | 12/1997 | Popov et al. |
| 5,755,775 | A | | 5/1998 | Trerotola et al. |
| 5,766,158 | A | | 6/1998 | Opolski |
| 5,779,731 | A | | 7/1998 | Leavitt |
| 5,792,095 | A | | 8/1998 | Kissinger et al. |
| 5,795,325 | A | | 8/1998 | Valley et al. |
| 5,797,879 | A | * | 8/1998 | DeCampli ................ 604/93.01 |
| 5,797,934 | A | | 8/1998 | Rygaard |
| 5,817,113 | A | | 10/1998 | Gifford, III et al. |
| 5,830,222 | A | | 11/1998 | Makower |
| 5,830,228 | A | | 11/1998 | Knapp et al. |
| 5,843,027 | A | | 12/1998 | Stone et al. |
| 5,868,770 | A | | 2/1999 | Rygaard |
| 5,893,369 | A | | 4/1999 | LeMole |
| 5,925,060 | A | | 7/1999 | Forber |
| 5,954,706 | A | | 9/1999 | Sahatjian |
| 5,961,536 | A | | 10/1999 | Mickley et al. |
| 5,976,178 | A | | 11/1999 | Goldsteen et al. |
| 6,007,576 | A | | 12/1999 | McClellan |
| 6,030,392 | A | | 2/2000 | Dakov |
| 6,042,569 | A | | 3/2000 | Finch, Jr. et al. |
| 6,063,114 | A | | 5/2000 | Nash et al. |
| 6,068,637 | A | | 5/2000 | Popov et al. |
| 6,086,553 | A | | 7/2000 | Akbik |
| 6,102,884 | A | | 8/2000 | Squitieri |
| 6,113,612 | A | | 9/2000 | Swanson et al. |
| 6,171,319 | B1 | | 1/2001 | Nobles et al. |
| 6,200,257 | B1 | | 3/2001 | Winkler |
| 6,210,365 | B1 | | 4/2001 | Afzal |
| 6,214,022 | B1 | | 4/2001 | Taylor et al. |
| 6,248,117 | B1 | | 6/2001 | Blatter |
| 6,254,563 | B1 | | 7/2001 | Macoviak et al. |
| 6,261,257 | B1 | | 7/2001 | Uffacker et al. |
| 6,264,633 | B1 | | 7/2001 | Knorig |
| 6,280,460 | B1 | | 8/2001 | Bolduc et al. |
| 6,293,965 | B1 | | 9/2001 | Berg et al. |
| 6,319,226 | B1 | | 11/2001 | Sherry |
| 6,401,721 | B1 | | 6/2002 | Maginot |
| 6,595,941 | B1 | * | 7/2003 | Blatter ...................... 604/4.01 |
| 6,656,151 | B1 | * | 12/2003 | Blatter .................... 604/96.01 |
| 6,663,590 | B1 | * | 12/2003 | Blatter .................. 604/103.01 |
| 6,746,459 | B1 | | 6/2004 | Kato |
| 2002/0049459 | A1 | | 4/2002 | Kato |

OTHER PUBLICATIONS

Clark Biocompatible Hemoperfusion System and Block Cutter, *Some Other Products from Clark Research, Clark® Biocompatible Hemoperfusion,* located at http://www.clarkrd.com/crd_other2.htm, 2pgs., printed Dec. 17, 1999.

HGSA Medicare Policy S-107: Hemoperfusion, *Medicare Medical Policy Bulletin, Freedom of Information,* located at http://www.hgsa.com/professionals/policy/s107.html, 1 pg., printed May 22, 2002.

Xact Medicare Services, Xact Medicare Policy S-53: Hemofiltration (Diafiltration) *Medicare Medical Policy Bulletin, Freedom of Information,* located at http://www.xact.org/policy/s107.html, 1 pg., printed Dec. 17, 1999.

Facts about Plasmapheresis, *Plasmapheresis and Autoimmune Disease,* MDA Publications, located at http://www.mdausa.org/publications/fa-plasmaph.html, 4 pgs., printed May 22, 2002.

Publications, *Hemodialysis,* located at http://www.kidney.ca/hme-e.htm, 4 pgs., printed May 22, 2002.

Tennessee Kidney Clinics and Affiliates, *What is Hemodialysis?* located at http://www.dialysisclinics.com/hemo.htm, 1 pg., printed May 22, 2002.

*Good Nutrition & Hemodialysis,* located at http://www.nyu.edu/classes/computrfood/Cecilia%20Fong/index.html, 1 pg., printed May 22, 2002.

Mulzer, S.R. and Brash, J.L., *Identification of Plasma Proteins Adsorbed to Hemodialyzers During Clinical Use,* Journal of Biomedical Materials Research, vol. 23, 1483-1504 (1989).

Ljungberg, B., et al., *Effective Anticoagulation by a Low Molecular Weight Heparin (Fragmin®) in Hemodialysis with a Highly Permeable Polysulfone Membrane,*Clinical Nephrology, vol. 38, No. 2-1992 (97-100).

Jen Ming Yang, et al., *Preparation of Heparin Containing SBS-g-VP Copolymer Membrane for Biomaterial Usage,* Journal of Membrane Science 138 (1998) 19-27.

Office Action dated Sep. 20, 2005 in U.S. Appl. No. 10/624,315, 7 pgs.

Interview Summary from Oct. 18, 2005 in U.S. Appl. No. 10/624,315, 1 pg.

Office Action Response dated Dec. 16, 2005 in U.S. Appl. No. 10/624,315, 19 pgs.

Office Action dated Sep. 29, 2005 in U.S. Appl. No. 10/624,711, 7 pgs.

Interview Summary from Oct. 18, 2005 in U.S. Appl. No. 10/624,711, 1pg.

Office Action Response dated Dec. 15, 2005 in U.S. Appl. No. 10/624,711, 16 pgs.

Office Action dated Jan. 12, 2006 in U.S. Appl. No. 10/351,172, 2 pgs.

Office Action Response dated Feb. 10, 2006 in U.S. Appl. No. 10/351,172, 12 pgs.

Office Action dated Aug. 18, 2005 in U.S. Patent Appl. No. 10/351,172, 5 pgs.

Interview Summary from Oct. 18, 2005 in U.S. Appl. No. 10/351,172, 1 pg.

Office Action Response dated Dec. 16, 2005 in U.S. Appl. No. 10/351,172, 21 pgs.

Office Action dated Jan. 29, 2002 in U.S. Appl. No. 09/481,283 (Patent No. 6,595,941), 7 pgs.

Interview Summary from Jun. 13, 2002 in U.S. Appl. No. 09/481,283 (Patent No. 6,595,941), 1 pg.

Office Action Response dated Jul. 1, 2002 in U.S. Patent Appl. No. 09/481,283 (Patent No. 6,595,941), 13 pgs.

Office Action dated Sep. 25, 2002 in U.S. Appl. No. 09/760,322 (Patent No. 6,663,590), 9 pgs.

Interview Summary from Nov. 21, 2002 in U.S. Appl. No. 09/760,322 (Patent No. 6,663,590), 1 pg.

Office Action Response dated Mar. 25, 2003 in U.S. Appl. No. 09/760,322 (Patent No. 6,663,590), 31 pgs.

Office Action dated Jun. 18, 2003 in U.S. Appl. No. 09/760,322 (Patent No. 6,663,590), 4 pgs.

Office Action Response dated Jun. 26, 2003 in U.S. Appl. No. 09/760,322 (Patent No. 6,663,590), 2 pgs.

Office Action (Election/Restrictions) dated Apr. 10, 2001 in U.S. Appl. No. 09/480,964 (Patent No. 6,656,151), 4 pgs.

Response to Restriction Requirement dated Jul 10, 2001 in U.S. Appl. No. 09/480,964, (Patent No. 6,656,151) 2 pgs.

Office Action dated Sep. 13, 2001 in U.S. Appl No 09/480,964 (Patent No. 6,656,151), 6 pgs.

Office Action Response dated Mar. 13, 2002 in U.S. Appl. No. 09/480,964 (Patent No. 6,656,151), 8 pgs.

Interview Summary from Mar. 13, 2002 in U.S. Appl. No. 09/480,964 (Patent No. 6,656,151), 1 pg.

Final Office Action dated Apr. 9, 2002 in U.S. Appl. No. 09/480,964 (Patent No. 6,656,151), 7 pgs.

Final Office Action dated Oct. 1, 2002 in U.S. Appl. No. 09/480,964 (Patent No. 6,656,151), 7 pgs.

Interview Summary from Nov. 21, 2002 in U.S Appl. No. 09/480,964 (Patent No. 6,656,151), 1 pg.

Office Action Response dated Apr. 1, 2003 in U.S. Appl. No. 09/480,964 (Patent No. 6,656,151), 36 pgs.

Interview Summary from May 6, 2003 in U.S. Appl. No. 09/480,964 (Patent No. 6,656,151), 1 pg.

* cited by examiner

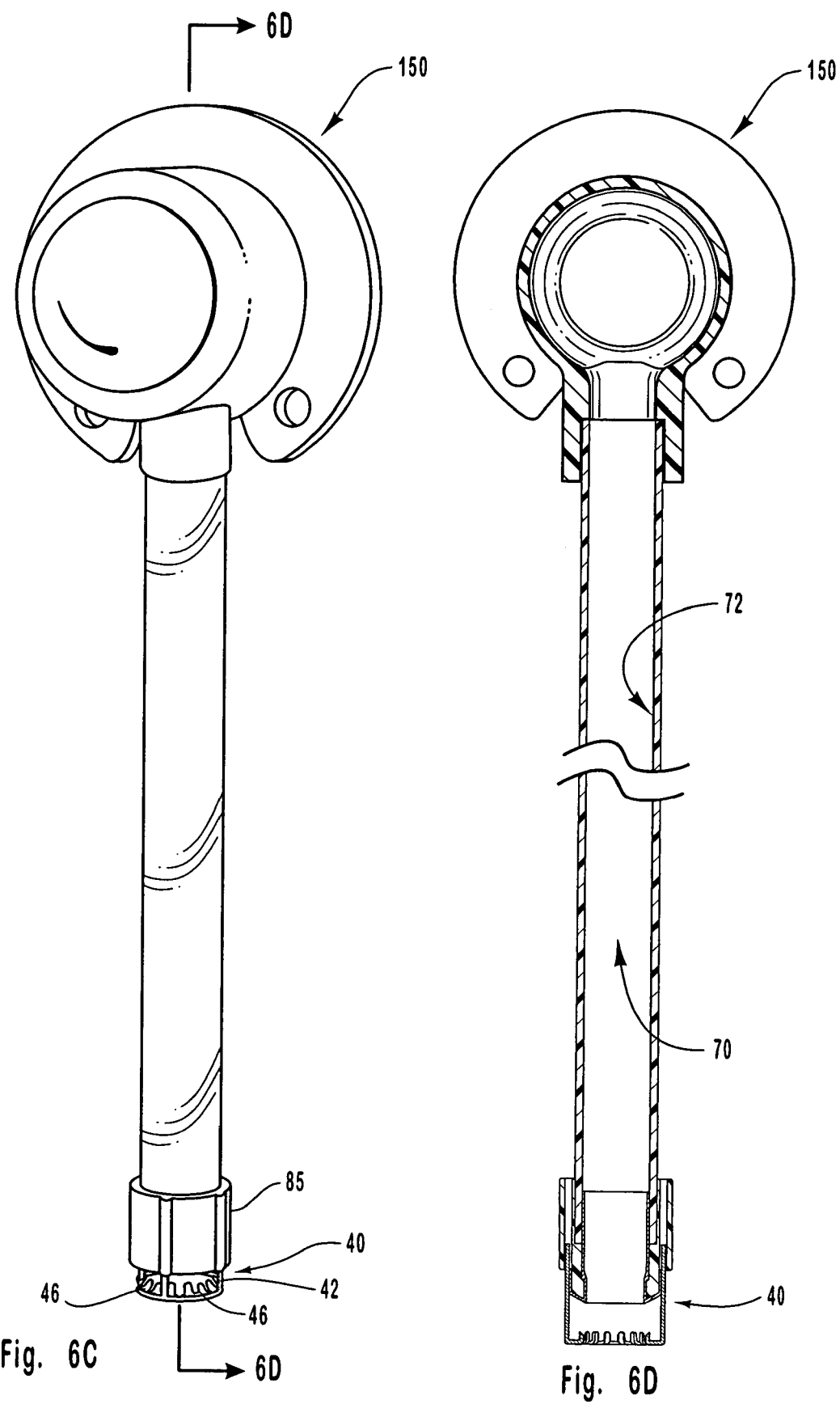

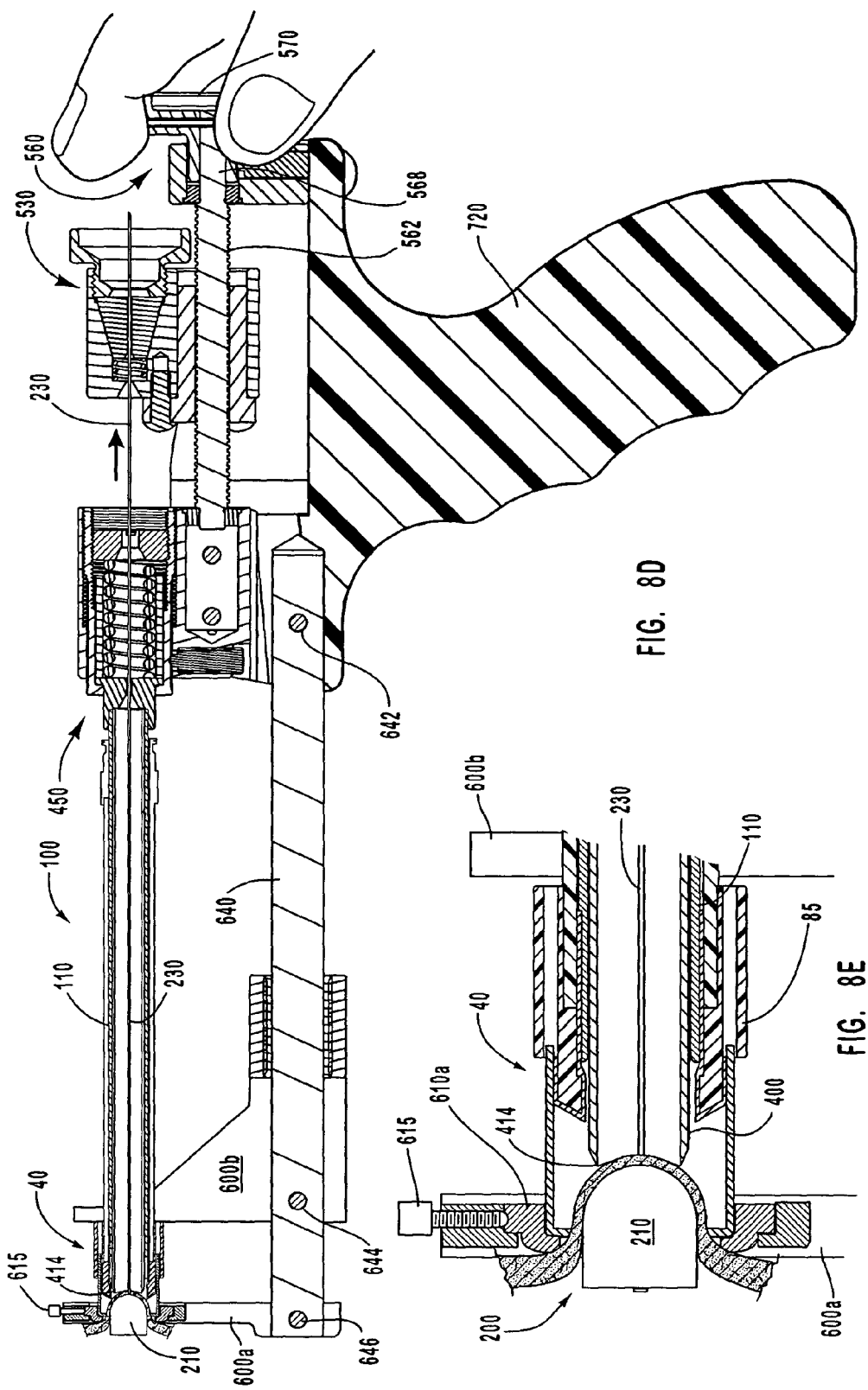

APPARATUS AND METHODS FOR FLUID OCCLUSION OF AN ACCESS TUBE ANASTOMOSED TO AN ANATOMICAL VESSEL

RELATED APPLICATIONS

This is a continuation-in-part of application Ser. No. 10/351,172, titled "Apparatus and Methods for Occluding an Access Tube Anastomosed to Sidewall of an Anatomical Vessel" and filed on Jan. 23, 2003. This Application is hereby incorporated by specific reference.

TECHNICAL FIELD

The present invention relates to vascular access methods and apparatus. More particularly, it relates to such methods and apparatus that allow for repeated access to an anatomical vessel such that repeated punctures of the vessel are not necessary.

SUMMARY OF THE INVENTION

The present invention provides methods and apparatus for facilitating long-term, repeated vascular access while minimizing the problems typically associated with such devices. By minimizing the surface area of non-native or externally introduced material exposed to blood flow in the vessels, and by making those surfaces that are exposed easily replaceable, many complications can be controlled or eliminated.

These objects are achieved by providing an access tube apparatus that is adapted for anastomosis to a target blood vessel. After an opening is formed in the target vessel, the access tube can be anastomosed to the vessel using any desired method, including suturing, stapling, clamping, welding, adhesives, etc. In one embodiment, the access tube has an attached or integrally formed anastomosis ring with guide posts fitting within slots in an attached or integrally formed portion of the access tube to facilitate the anastomosis procedure. Once anastomosed to the target vessel, the access tube apparatus may extend through the patient's skin with an access end that is percutaneously accessible or it may be configured such that the entire device is positioned subcutaneously.

Fitting within the conduit of the access tube is a fluid that serves as an occluder to block fluid communication from the target vessel lumen to the access tube. Available fluids for use as an occluder range from viscous fluids, such as gels, hydrogels and the like, to less viscous fluids, such as saline solutions and the like.

The access tube has an access cap and/or a self-sealing access port through which to withdraw and insert the fluid occluder. The access cap and/or access port may also be used to gain access to the body fluid inside the target vessel. Once the access end of the access tube is closed, the fluid occluder is substantially prevented from entering the target vessel lumen by a vacuum in the access tube behind the fluid occluder, and the body fluid in the target vessel is thereby substantially kept from entering the access tube by the fluid occluder. However, it should be understood that there will typically be some migration of blood into the fluid occluder, and vice-versa, at the interface site between the two.

Optionally, pharmacological agents may be incorporated into the fluid occluder and/or applied to surfaces inside the access tube conduit. For instance, substances that include pharmacological agents such as antibacterial, antithrombotic, or antiproliferative agents may be added to the fluid occluder to control complications at the anastomosis site. One or more of the same substances may be applied as a coating to the interior wall of the access tube.

One method of the present invention utilizes two of the access tube devices discussed, one being used for extracting blood from the target vessel and the other used for inserting treated blood back into the blood stream. The second access tube used to insert the treated blood can be anastomosed to the same target vessel at another location or, alternatively, it can be anastomosed to a different blood vessel. Of course, whereas the device is typically used in connection with blood vessels, it may also be effectively employed in connection with other anatomical vessels, such as ureters/urethra, or any other anatomical vessel.

While two access tubes are typically used, it is also possible to use a single access tube. For example, only one access tube would be necessary for withdrawing particularized amounts of blood or other body fluid for testing, etc., or for inserting medications or other pharmacological agents into a patient's bloodstream. A single access tube could also be used intermittently to both withdraw and insert blood for treatment. Alternatively, a single multi-lumen tube could be used to withdraw and insert blood simultaneously.

Additional aspects and advantages of this invention will be apparent from the following detailed description of preferred embodiments, which proceeds with reference to the accompanying drawings.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 6C is a perspective view of the access tube device with an access port attached thereto.

FIG. 6D is a cross-sectional view of the access tube device shown in FIG. 5C.

FIG. 8D is a cross-sectional view of the external anastomosis operator.

FIG. 8E is a partial cross-sectional view of the external anastomosis operator engaging the anvil apparatus inside the target blood vessel during an anastomosis procedure.

DETAILED DESCRIPTION OF PREFERRED EMBODIMENTS

Figure 1:
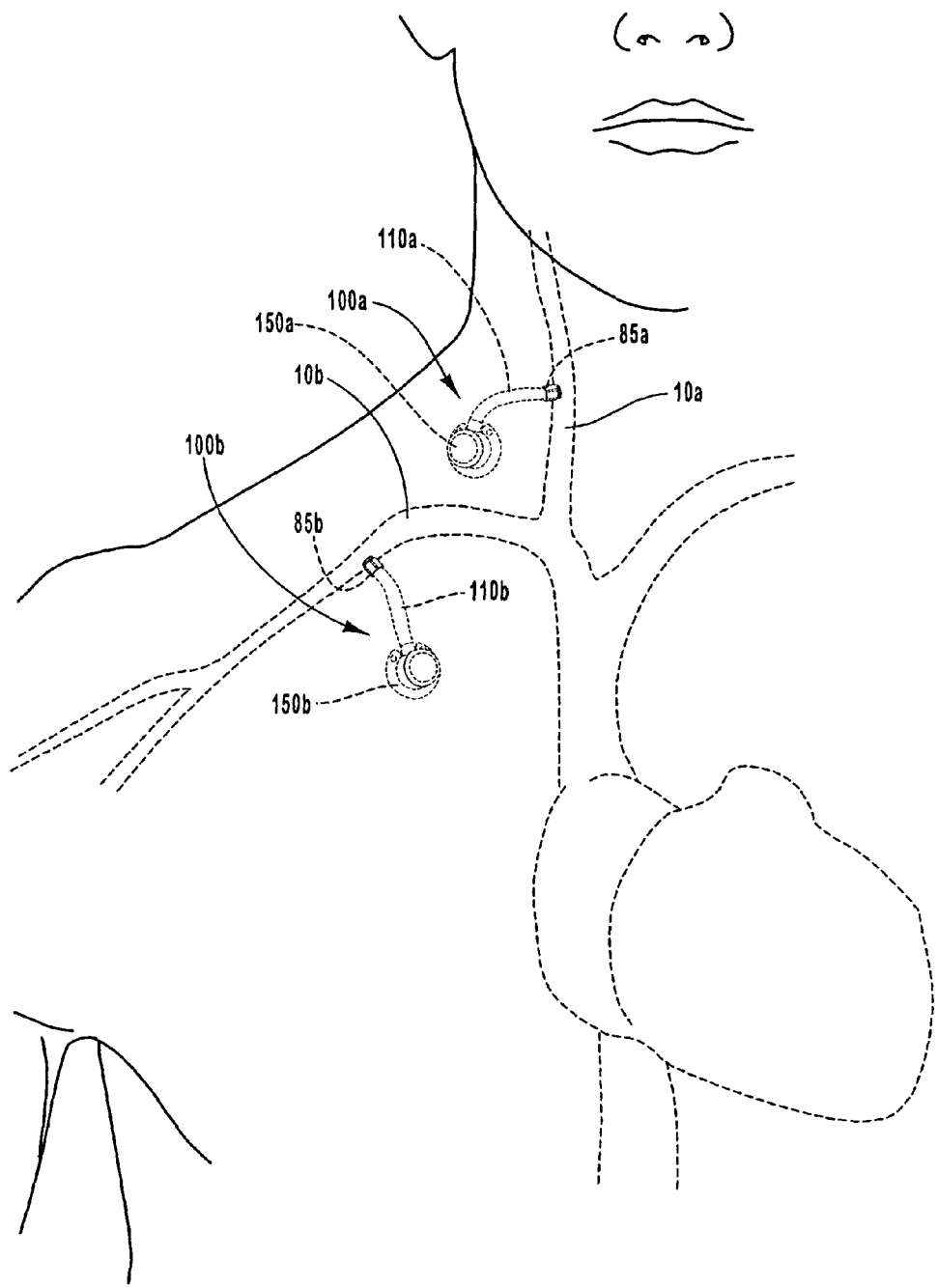
FIG. 1 is a perspective view of two access tube devices attached to a patient's blood vessels.

The method of the present invention involves the use of an occludable access tube apparatus to facilitate repeated access to a body fluid in an anatomical vessel. The apparatus is adapted for anastomosis to a vessel, and is occluded between vessel accesses with a fluid suitable for use as a fluid occluder.

The main components of one embodiment of the occludable access tube apparatus 100 include an access tube and a fluid occluder. The access tube is adapted for anastomosis to an anatomical vessel at an anastomosis end of the access tube. Examples of access tubes are shown in the figures at 110 (110a and 110b for systems including two access tubes). Examples of fluid occluders are identified at 90. As explained in greater detail below, fluids available for use as a fluid occluder range from viscous fluids, such as gels or hydrogels, to less viscous fluids, such as saline solutions.

The anastomosis procedure is typically facilitated by the use of an anastomosis component. In one embodiment, apparatus 100 includes an anastomosis component referred to as a target vessel anastomosis ring. One example of a target vessel anastomosis ring is shown in the accompanying figures at 40. The target vessel anastomosis ring may be adapted to cooperate with an access tube anastomosis ring, identified generally at 85, in accomplishing the anastomosis procedure. Target vessel anastomosis ring 40 and access tube anastomosis ring 85 are best seen in FIGS. 3B, 6B, and 7A–7F. It is preferable that the anastomosis is accomplished such that, once the fluid occluder is positioned within the access tube, exposure of the blood or other body fluid in the target vessel to non-native materials is minimized. "Non-native" materials, as the term is used herein, are those materials that have been introduced into the patient as part of the disclosed procedures—i.e., they are foreign materials that were not already present in the patient before introducing the access tube apparatus.

Another component in some embodiments is an access port that is in fluid communication with the access tube. Examples of access ports are shown at 150. Access tube 110 has an access end opposite from its anastomosis end that is adapted to be fit with either an access port device or an access cap. Most of the embodiments depicted in the accompanying figures are shown fitted with a self-sealing access port 150.

As discussed in much greater detail below, some embodiments of the method of the invention involve the use of two separate occludable access tube apparatus 100. In such embodiments, one access tube apparatus is used to extract a body fluid and another is used to insert a body fluid. The components associated with the extraction device are labeled in the accompanying figures with a suffixed "a" and the components associated with the insertion device are labeled with a suffixed "b."

FIG. 1 shows two separate access tubes anastomosed to the sidewalls of two separate target blood vessels, identified at 10a and 10b in the figure. The anastomosis of the access tubes to the vessels can be done by any suitable methodology, including suturing, stapling, welding, clamping, use of adhesives, anastomosis rings and/or plates, or any other anastomosis technology currently known in the art or hereafter developed. However, in the embodiment depicted in the accompanying figures, an anastomosis ring is used, which is attachable to the access tube device, in combination with another similar ring attached to, or integrally formed with, the access tube. The method for deploying this embodiment involves the use of an external anastomosis operator. The anastomosis rings and the external operator are discussed in greater detail later in relation to the access tubes.

Figure 3A:
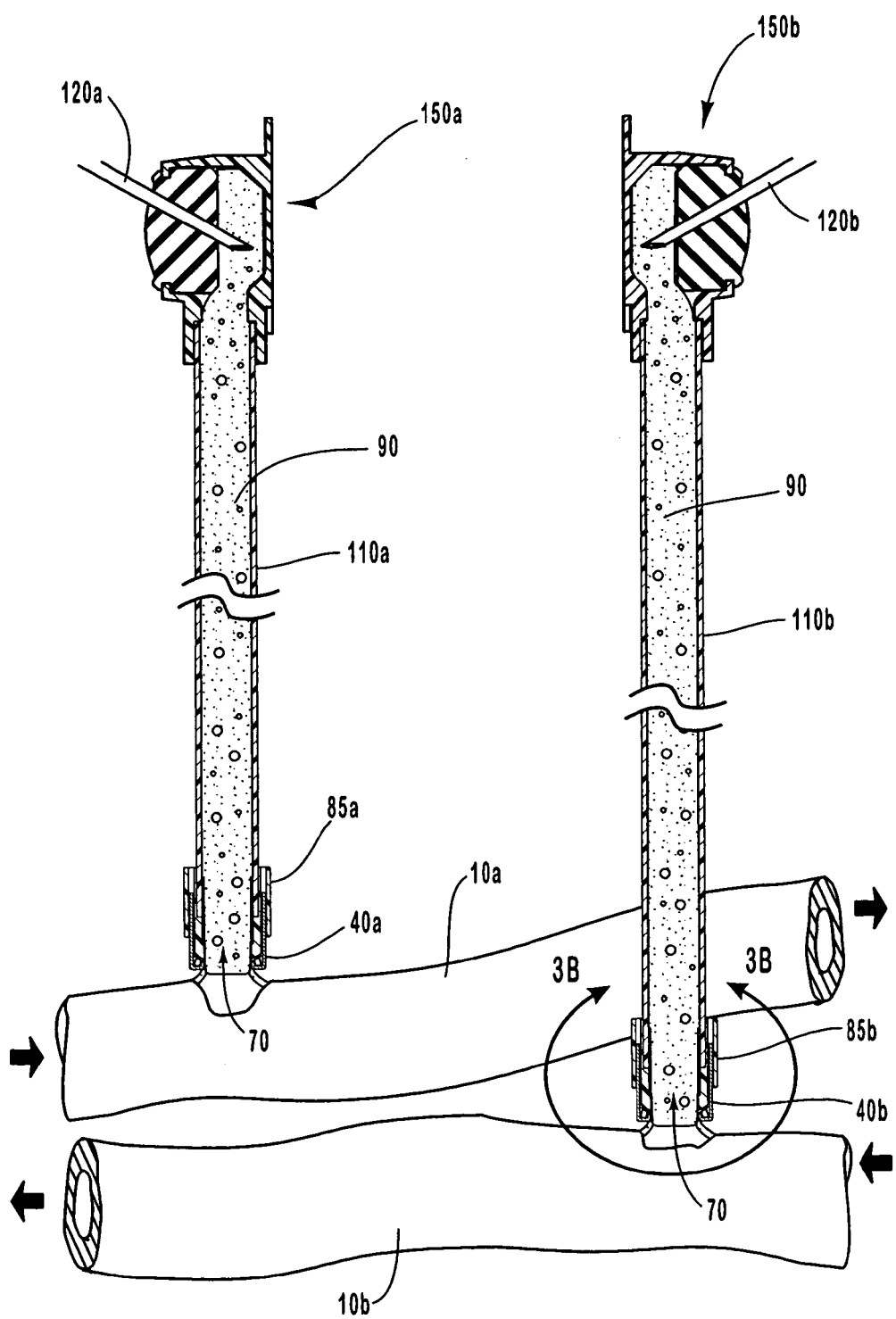
FIG. 3A is a partial cross-sectional view of the access tube devices with needles penetrating their respective ports to insert the fluid occluder.
Figure 3B:
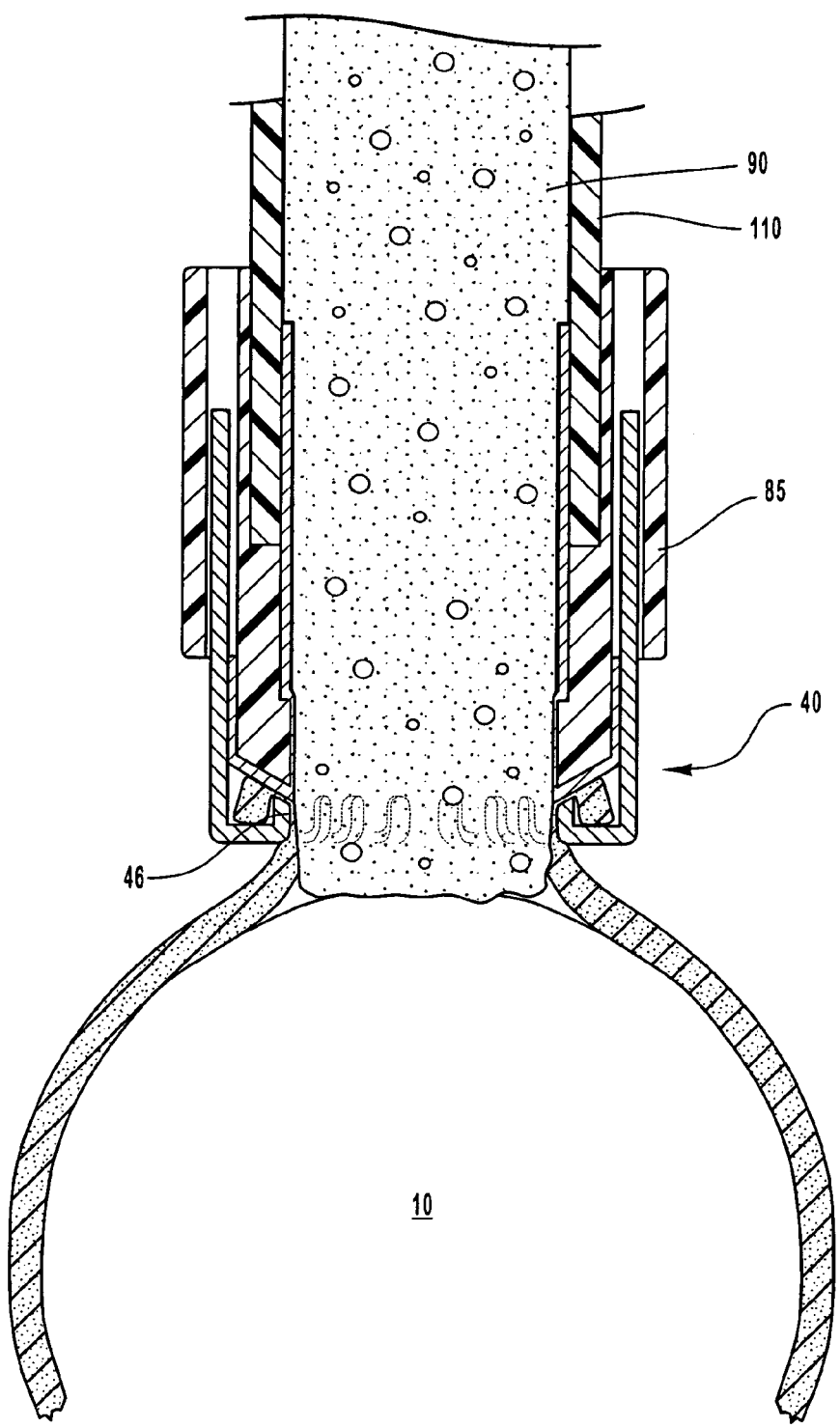
FIG. 3B is an enlarged cross-sectional view of the interface between the occlusion end of an occluded access tube device and the target vessel wall.

Regardless of the methodology used to attach the access tube to the target vessel, however, it is preferable that the access tube not extend significantly into the target vessel lumen so as to disrupt the flow of blood or other body fluids in the vessel lumen. Accordingly, as the term is used in this context, an access tube can extend into a target vessel without extending "significantly" therein if the flow of body fluid in the access-tube region is not disrupted to the degree that it would tend to cause complications. FIG. 3B depicts an embodiment of the invention with an access tube that does not extend at all into the target vessel lumen. Note, however, that the access tubes of other embodiments may extend slightly into the target vessel lumen and still be considered to not extend significantly therein. While an access tube in accordance with the invention may still extend slightly into the target vessel lumen, it should not extend into the lumen to a degree such that the cross-sectional area of the lumen near the access tube is decreased significantly. Moreover, the access tubes of some embodiments may not be flush with the remainder of the target vessel wall, and yet are still able to avoid extending significantly into the target vessel lumen.

Some embodiments of the device may sit recessed from adjacent portions of the target vessel so as to stretch the target vessel somewhat. Other embodiments may be configured such that the device is offset or recessed from the stream of body fluid in the lumen, as shown in FIG. 3B. While not depicted, it is possible that some other embodiments may sit against the target vessel so as to deform the target vessel lumen radially inward. In other words, the device may deform the target vessel by compressing the vessel from the outside while still avoiding extending into the target vessel. The device, however, should not deform the target vessel lumen to the extent that that complications arise due to constriction of the vessel lumen.

While FIG. 1 shows the access tubes attached to blood vessels, the present invention can be used in connection with any anatomical vessel. To illustrate, the devices, methods, and systems disclosed herein may be used in connection with ureters, urethras, intestines, or any other vessel in the body. Thus, the present invention can provide access to body fluids other than blood. In fact, any body fluid within any anatomical vessel can be accessed by the herein disclosed apparatus, methods, and systems.

The first access tube apparatus, or extraction access tube apparatus 100a, is attached to first target blood vessel 10a and extends to a desired subcutaneous location such that its access port is positioned just below the skin. Likewise, the second access tube apparatus, or insertion access tube apparatus 100b, extends from second target blood vessel 10b such that its access port is also positioned just below the skin. As should be apparent to one of skill in the art, the access ports may be configured to allow for suturing or other suitable methods for securing it to the patient's tissue.

Figure 4:
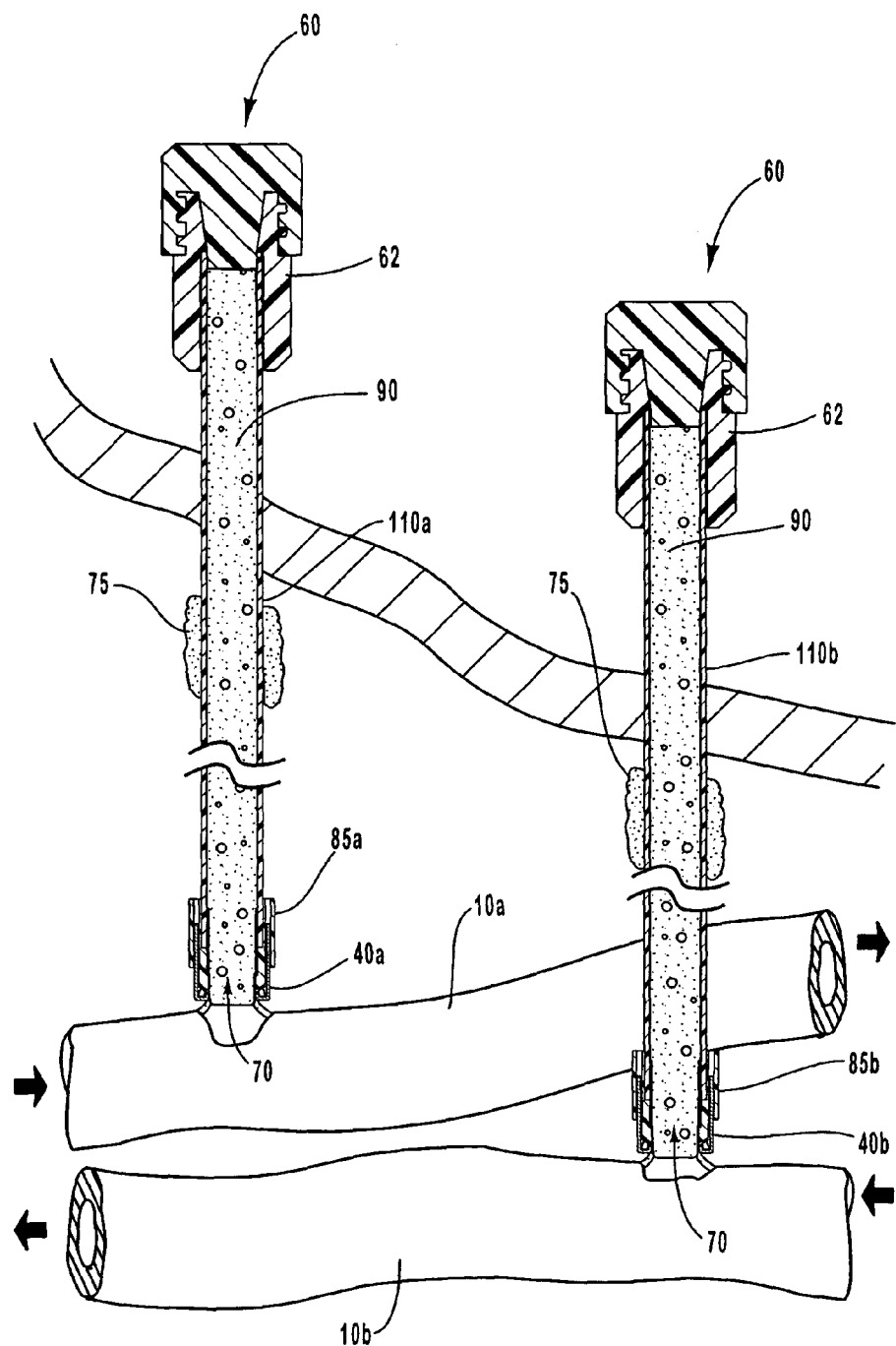
FIG. 4 is a partial cross-sectional view of extracorporeally accessible embodiments of the access tube devices.

Also, while the accompanying figures show the access tube devices positioned subcutaneously, this aspect of the invention should not be considered limiting. In other words, the devices could easily be positioned such that the access tubes extend percutaneously and are extracorporeally accessible, as shown in FIG. 4. In such embodiments, it may be preferable to replace the access port with an access cap 60, such as those disclosed in U.S. patent application Ser. No. 10/351,172, titled "Apparatus and Methods for Occluding an Access Tube Anastomosed to Sidewall of an Anatomical Vessel" and filed on Jan. 23, 2003, which is hereby expressly incorporated by reference in its entirety. Alternative access ports can be found in U.S. patent application Ser. No. 09/760,322 titled "Vascular Occlusal Balloons and Related Vascular Access Devices and Systems" and filed on Jan. 11, 2001, which is also hereby incorporated by reference in its entirety. Access caps and access ports as discussed herein are examples of port means for accessing the access tube means.

Figure 2:
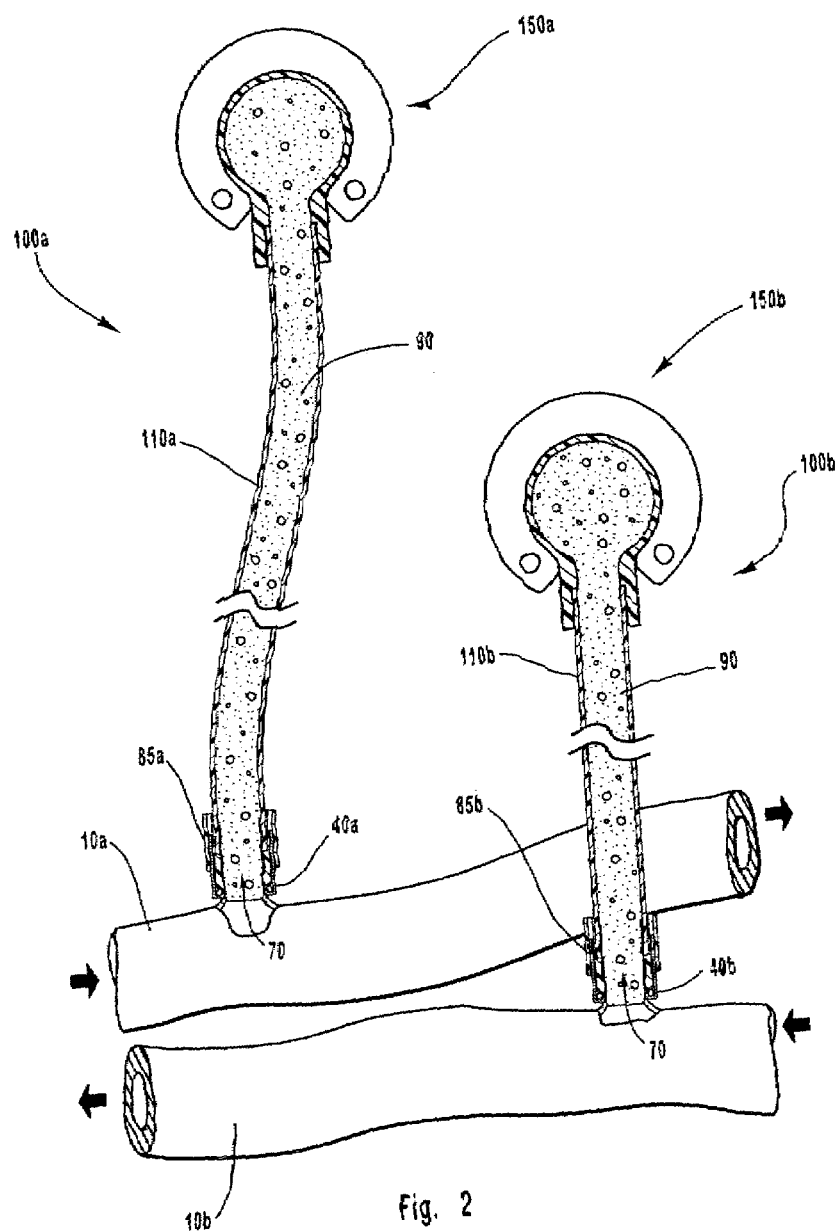
FIG. 2 is a partial cross-sectional view of the access tube devices with fluid occluders inside their respective access tubes and attached to separate blood vessels.

When access to the blood is not needed, and as best seen in subsequent figures beginning with FIG. 2, a fluid is inserted into the access tube conduit to be used as a fluid occluder 90. The fluid occluder 90 blocks fluid communication between each of the vessels and the access tube conduits. In this way, when access to the blood or other body fluid inside the target vessel is desired for treatment or any other reason, one need only remove the fluid serving as a fluid occluder from the access tube conduits to gain access.

As should be apparent, the present invention allows for enormous flexibility in the placement positions of the access tubes. While the embodiment shown in FIG. 1 has the extraction access tube apparatus 100a anastomosed to the jugular vein in the patient's neck and the insertion access tube apparatus 100b anastomosed to the subclavian vein, countless variations are possible. To illustrate, each of the access tubes could be anastomosed to any of the various other veins and/or arteries of the body, such as those in the arms, legs, shoulders, neck, or elsewhere.

Figure 5:
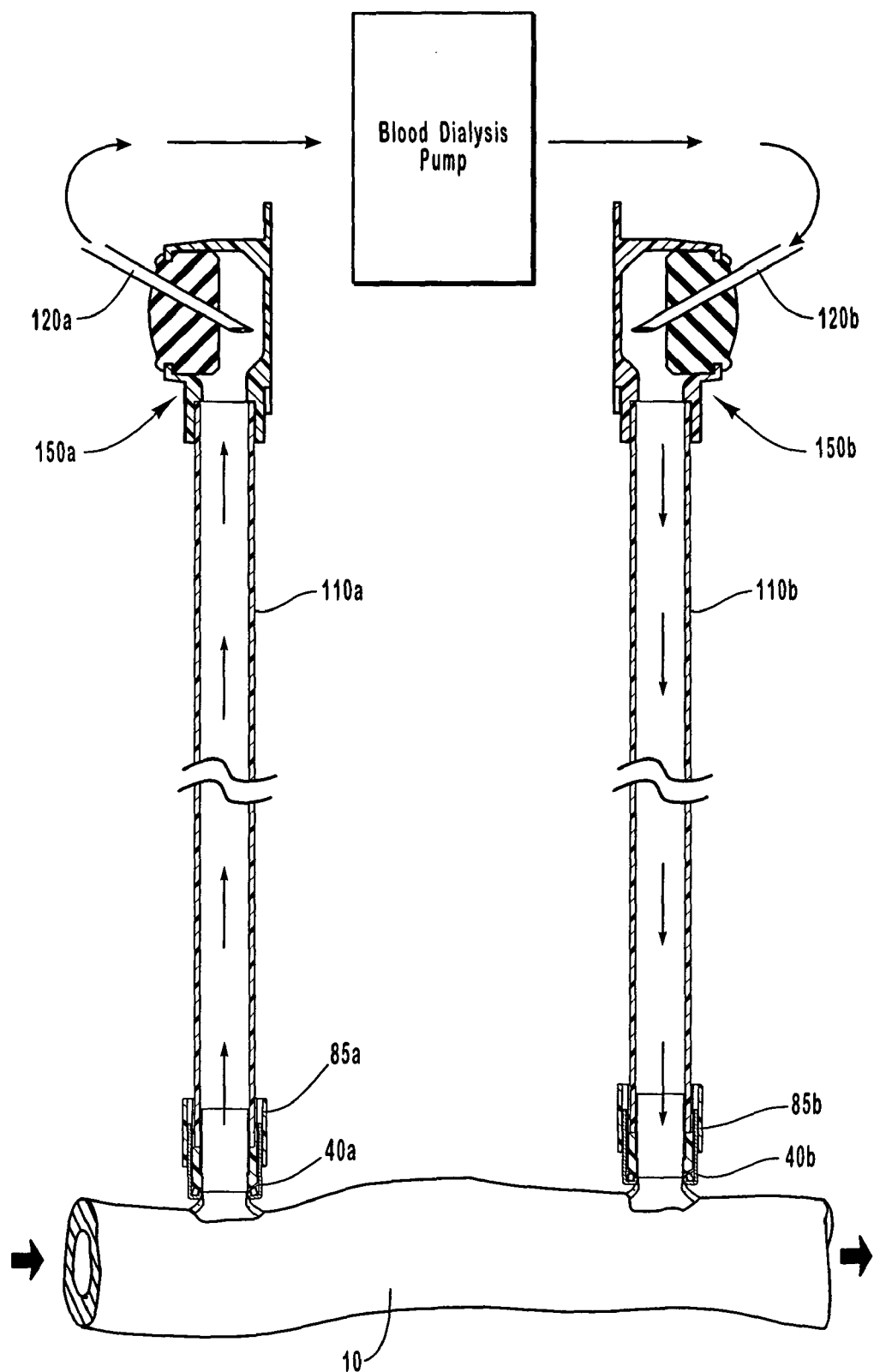
FIG. 5 is a partial cross-sectional view of the access tube devices attached to the same target vessel at two separate locations, again with the fluid occluders removed to allow for vascular access.

Moreover, the access tubes of the invention need not even be attached to separate vessels. FIG. 5 shows another embodiment of the occludable access tube apparatus wherein the extraction access tube apparatus and the insertion access tube apparatus are anastomosed to the same vessel 10 at separate locations, one downstream from the other. It should now be apparent that the precise location and type of vessel to which the device may be anastomosed may vary considerably without departing from the scope of the invention.

In FIG. 2, each of the two access tube devices is shown at its anastomosis site with a fluid occluder 90 filling its respective access tube conduit. The devices are fitted with self-sealing access ports 150a and 150b, respectively, to be described in greater detail later. While the embodiments disclosed in the accompanying figures include access ports, it should be apparent that many variations are possible, some of which do not utilize access ports. For instance, it may be desirable in certain circumstances, as indicated above, to replace the access port with an access cap, which may be configured to allow for a snap-fit, threaded, friction-fit or other suitable junction with the access tube. In particular, such a configuration may be desirable for embodiments wherein the access tubes are extracorporeally accessible as depicted in FIG. 4.

Figure 3C:
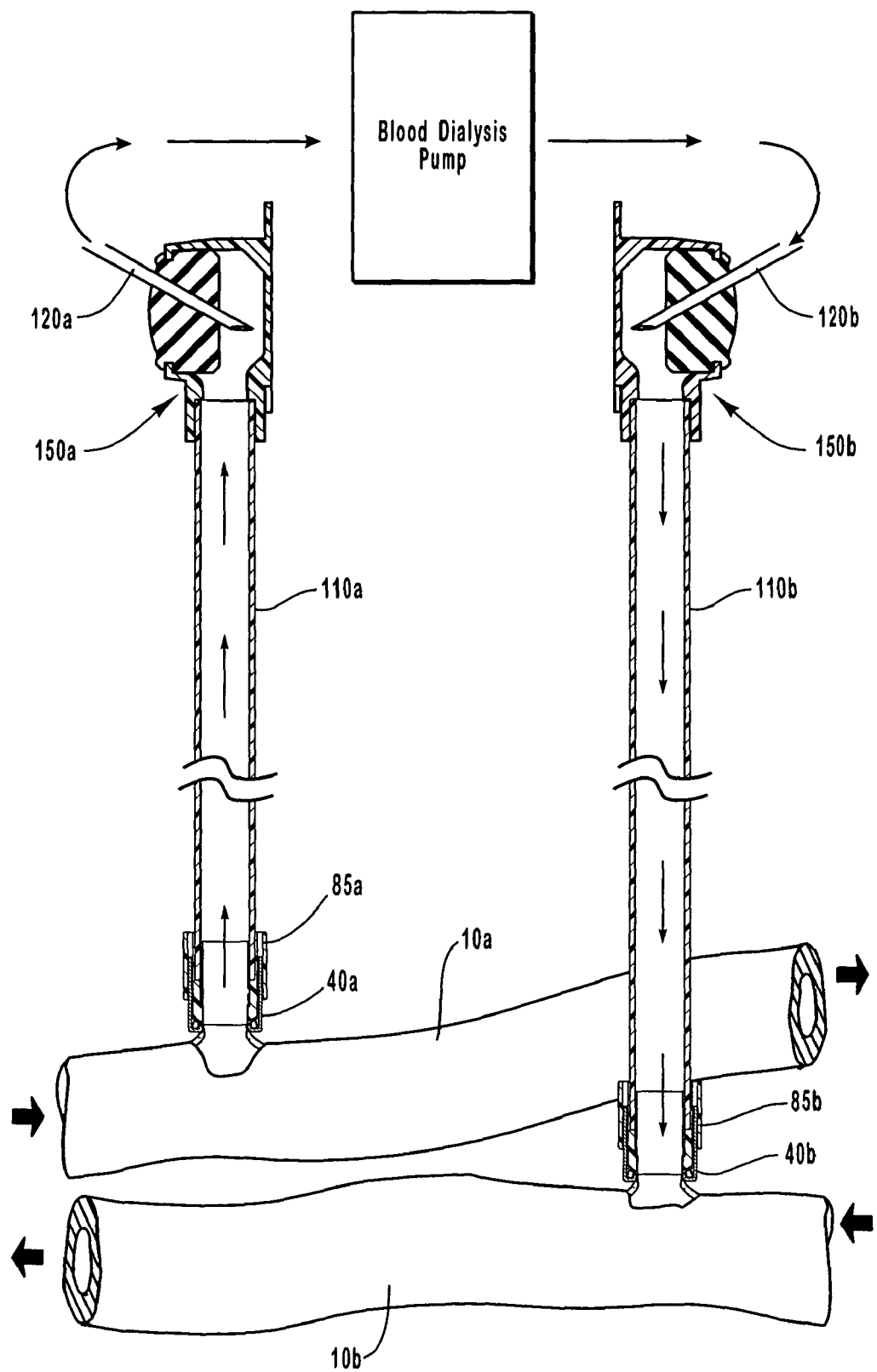
FIG. 3C is a partial cross-sectional view of the access tube devices after the fluid occluder has been removed to allow for access to the body fluid.

Access port 150 may be penetrated by a hypodermic needle 120 or any other medical instrument that can be used to inject and/or withdraw fluid. Such medical instruments may be used to insert the fluid occluder 90 into the access tube conduit 70, as shown in FIG. 3A, withdraw the fluid occluder 90 when vascular access is needed, and to withdraw blood or other body fluids for treatment, as shown in FIG. 3C. Of course, the fluid occluder may be inserted into the access tube conduit by any available means.

For instance, referring now to FIG. 4, for embodiments in which the access end of the access tube is extracorporeally accessible, and in which the access port is replaced with an access cap 60, the access cap may simply be removed and the fluid occluder inserted by any means available to one of skill in the art. Note that cap 60 in FIG. 4 is shown with an adapter 62 configured with threads for threaded engagement with cap 60. Adapter 62 may also be an integral extension of access tube 110. Of course, any suitable means for connecting access cap 60 to access tube 110 may be used in place of adapter 62. It may also be useful in extracorporeally accessible embodiments to provide for a pinch valve or other valve to help control the flow of the fluid occluder while the access end of the access tube is open. Alternatively, a device may be employed that periodically and incrementally pushes fluid occluder out of the access tube and into the vessel. Fluid occluder may then be re-inserted into the access tube at certain intervals to maintain the barrier between the body fluid and the access tube.

Because the access port 150 is self-sealing, the end of the access tube opposite from the anastomosis end 80 is sealed off as soon as the instrument used to insert the fluid occluder 90 has been withdrawn. A self-sealing access port can comprise any port device used to repeatedly isolate the conduit from external pressure (outside of the vascular system) to allow an attached access tube to contain fluid when the port is not penetrated and provide fluid communication to the conduit when a needle or other access device penetrates into the access port. A port may be self-sealing by virtue of having a penetrable septum or barrier that seals around a needle during access and seals shut upon withdrawal of the needle. Alternatively, a port may be self-sealing by virtue of having a valve structure performing the above-stated functions. One example of a self-sealing access port employing a valve structure is disclosed in U.S. Pat. No. 6,007,516 issued to Burbank et al., the disclosure of which is hereby incorporated by reference in its entirety.

Because the access end of the access tube remains closed during the time in between vascular accesses, a vacuum is created at the access end of the access tube conduit. In other words, the enclosed conduit holds the fluid occluder in place. As soon as any fluid occluder leaks out of the access tube, a vacuum is created by the void. This vacuum helps keep the fluid occluder 90 inside the access tube conduit 70.

FIG. 3B shows a close-up of the interface between the access tube apparatus and the target vessel. FIG. 3B shows a sufficient amount of fluid occluder 90 inserted into the access tube conduit such that the interface between the fluid occluder 90 and the body fluid inside vessel 10 is approximately flush with the native vessel wall. At this interface, the surface tension of the fluid occluder helps prevent body fluid from entering the access tube conduit, and vice-versa. However, it is understood that there will typically be some intermixing between the body fluid and the fluid occluder 90 at the interface. Accordingly, the present invention can function without rigidly maintaining the barrier between the body fluid and the fluid occluder 90. It is understood and expected that some of the fluid serving as fluid occluder 90 will enter the patient's bloodstream or other vascular system and likewise some of the patient's blood or other body fluid will enter into the access tube and intermix with the fluid occluder.

A variety of fluids may be suitable for use as a fluid occluder. Such fluids may range in viscosity from near water to near solid. Viscous fluids, such as gels or hydrogels and the like may be used. One or more polymers may also comprise the fluid occluder. Additionally, the fluid occluder may be a combination of gels and/or polymers.

One type of suitable polymer may have a propensity for high biocompatibility as well as modulated biodegradability. Another desirable characteristic of polymers used as fluid occluders or incorporated with fluid occluders is small molecular weight. For example, the molecular weight may be sufficiently small such that the polymer is exerted from the kidneys without accumulation toxicity becoming a problem. Polymers with a molecular weight of less than about 50,000 typically avoid such accumulation toxicity.

One group of polymers considered to possess desired properties for use in fluid occluders is polylactide (PLA). The properties of PLA may be modulated by copolymerization of lactide with other monomers including glycolide. PLA also has a molecular weight of approximately 10,000 and thus will not accumulate in the bloodstream when the device is used in connection with blood vessels.

Another polymer considered to have a desirable molecular weight is polyethylene glycol (PEG). PEG is a non-toxic water soluble polymer which resists recognition by the immune system and exhibits rapid clearance from the body. Because of these properties, fluid occluders prepared from PEG are useful fluid occluders. PEG may also transfer its properties to another molecule when it is covalently bound to that molecule and thus may be used in combination with other polymers or substances to produce a suitable biocompatible occluding fluid. Variants of PEG include poly(ethylene glycol) monomethacrylate (PEGMA) and poly(ethylene glycol) dimethacrylate (PEGDMA). PEG, PEGMA, and PEGDMA can be obtained commercially from such firms as Shearwater Polymers of Huntsville, Ala. and Polysciences Inc. of Warrington, Pa.

Additional examples of fluids potentially available for use as a fluid occluder include hydrogels such as Surgilube® gel, a registered trademark of E. Fougera & Co., a division of Altana, Inc. of Melville, N.Y. containing Chlorhexidine Gluconate and Hypan SA100H produced by Hymedic International, Inc. of Dayton, N.J. Still other examples of substances potentially useful in fluid occluders include polyesters, poly(orthoesters), polyanhydrides, polyamino acid, polyalkyl cyanoacrylates, polyphophazenes, copolymers of (PLA/PGA), and aspirate or Poly(ethylene oxide) PEO.

Less viscous fluids may also be used, such as saline solutions and the like. Depending upon the substance used, the fluid occluder may also expand when in contact with water. In such embodiments, the occluding fluid will continually expand such that the layer of fluid occluder adjacent to the body fluid will erode out into the stream of fluid in the anatomical vessel. This provides a continually renewing surface and a mechanism to keep the interface between the body fluid and the fluid occluder from retracting back into the access tube.

Each of the foregoing are examples of fluid occluding means for occluding an access tube means. Obviously, the type of fluid used to occlude the access tube should not be considered as limiting the scope of the invention.

In order to reduce the likelihood of infection, thrombosis, and other complications, the fluid occluder 90 may have pharmacological agents incorporated therein. Such agents include, but are not limited to, antibacterial agents to prevent infection, antithrombotic agents to prevent thrombosis formation, and/or antiproliferative agents to prevent neo-intimal hyperplasia or other potential problems. One or more of these agents can also be used as a coating on the interior wall 72 of the access tube conduit 70. A typical agent used for these purposes is an anticoagulant such as heparin or modified heparin compounds such as Duraflow II produced by Edwards Life Sciences. Antibacterial agents that have been shown to provide an effective short-term infection barrier when applied as a coating include chlorhexadine and silver sulfadiazine. Drug-eluting coatings containing antiproliferative agents, such as paclitaxel, have been shown to be beneficial in preventing restenosis due to neo-intimal hyperplasia. However, any pharmacological substance known to those skilled in the art now or hereafter could be used as a coating and/or incorporated into the fluid occluder 90.

When access to the vessel is desired, the fluid may then be withdrawn from the access tube conduit 70. This may be accomplished in any number of ways. For instance, for embodiments including an access port, the fluid may be withdrawn with a hypodermic needle 120 via the port. Then, vascular access may be obtained by again inserting a needle or other suitable medical device into the access port.

In FIG. 3C the access tubes are shown with needles 120a and 120b, respectively, inserted into their access ports 150a–b and with their fluid occluders removed to allow for vascular access for blood treatment. As the arrows in the figure indicate, blood flows from blood vessel 10a into the access tube conduit 70 of occludable extraction access tube apparatus 100a and is drawn to a blood treatment device with a needle or other extraction device. The blood treatment device is most typically a hemodialysis machine, but it can be any device capable of performing blood treatment of any kind outside a patient's body. Moreover, because the invention is suitable for use in providing access to body fluids other than blood, the treatment device can be any device capable of performing treatment on any such body fluid accessed by the methods and appartus of the invention. Of course, for other uses of the invention, a treatment device need not even be used. For instance, access to a body fluid may be needed for obtaining samples of the fluid, or for inserting medications or other substances into the vascular system. However, when a treatment device is used, as shown in FIG. 3C, after the blood has been treated it is inserted into access tube conduit 70 of occludable insertion access tube apparatus 100*b* via another needle 120*b* or other insertion device. The blood then re-enters the patient's bloodstream through blood vessel 10*b*.

Once access to the vascular system of the target vessel is no longer needed, needles 120 are re-inserted into the self-sealing access ports 150 of the two access tube devices to re-insert the fluid to be used as the fluid occluder 90. Once the fluid has filled the access tube conduits such that the blood/occluding-fluid interface is near the native vessel wall, as shown in FIGS. 3A–3B, the needles can be withdrawn until further treatment is needed.

Referring now to FIG. 5, the extraction access tube apparatus is anastomosed to blood vessel 10, and the insertion access tube apparatus is anastomosed to the same blood vessel 10 at a downstream location. Otherwise, the apparatus shown in FIG. 5 is identical to that shown in FIGS. 2–3C. Again, as indicated by the arrows, blood from blood vessel 10 is drawn through access tube conduit 70 of access tube 110*a* and into a blood treatment device by using a needle 120*a*, after which it is re-inserted into blood vessel 10 through access tube conduit 70 of access tube 110*b*, again by using a needle 120*b*.

Figure 6A:
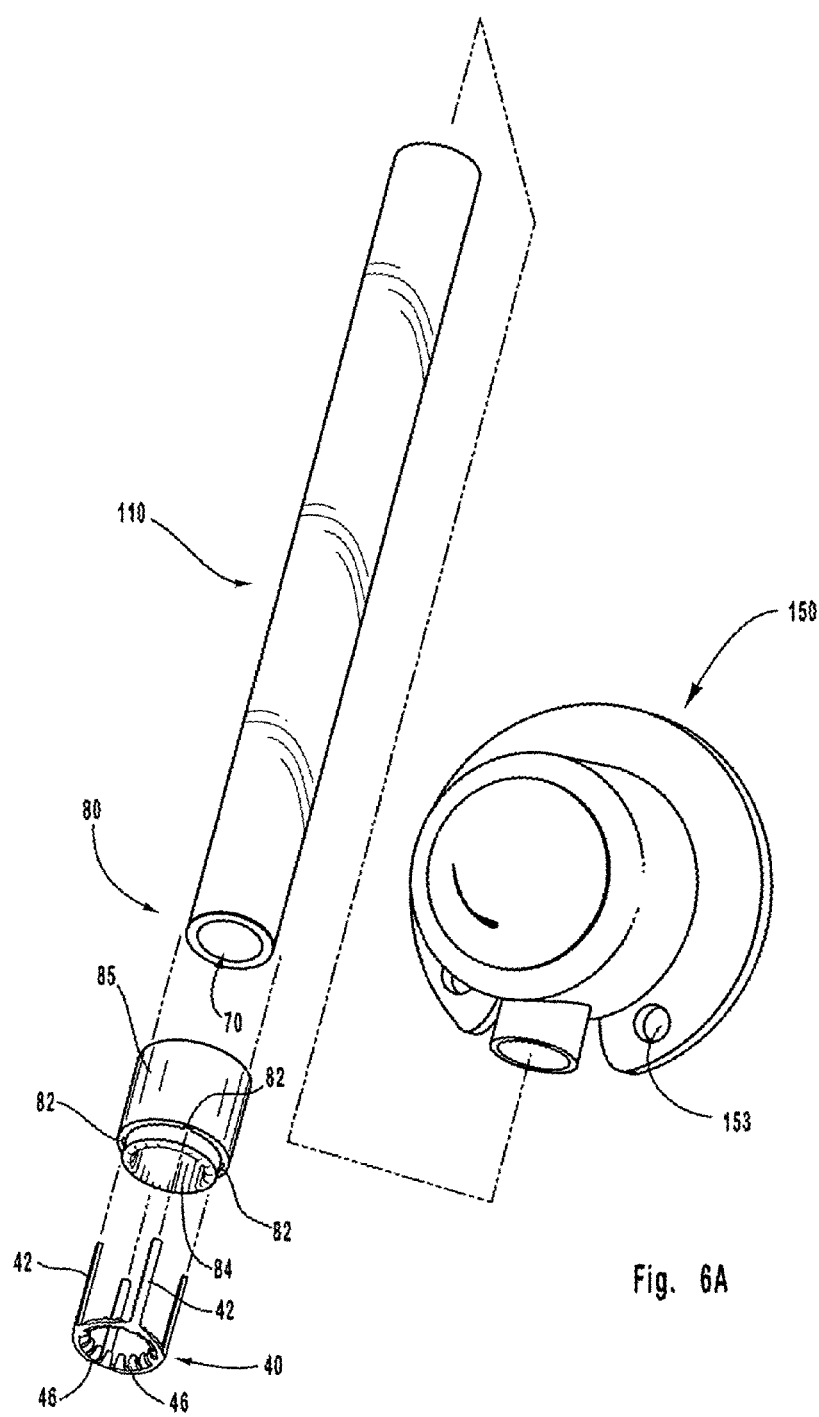
FIG. 6A is an exploded perspective view of the access tube device with the access port removed and the target vessel anastomosis ring withdrawn from the slots in the access tube anastomosis ring.

FIG. 6A provides a more detailed depiction of the embodiment of the access tube apparatus of the present invention. Access tube 110 has an anastomosis end 80 opposite from an end adapted to be fit with a port device 150. A conduit 70 extends from the anastomosis end 80 to the opposite end. The access tube 110 and conduit 70 therein can be of any cross-sectional shape and size. Moreover, the term "access tube" is meant to encompass any of various known or hereafter known suitable devices, including graft vessels, catheters, and the like. These are all also examples of access tube means for accessing an anastomosed vessel.

An anastomosis component, such as an anastomosis ring, plates, etc., can facilitate the attachment of the access tube to the target vessel. Alternatively, the access tube can have preformed holes at the anastomosis end for suturing. Yet another alternative is an access tube that is soft enough to be punctured by standard suturing procedures, such as a graft vessel. The portion of the access tube defining the conduit 70 is typically made of a flexible and blood-compatible material, such as polyurethane or silicone. However, it could be made of any other blood-compatible material.

Although not necessary, using a flexible material to form the portion of access tube 110 defining the conduit 70 may be desirable for a number of reasons. In embodiments in which the access tube protrudes from the skin, providing a flexible access tube allows the extracorporeally accessible portion of the tube to be flexed and pressed against the skin, perhaps even affixed to the skin, when not in use. This contributes to the inconspicuousness of the device and for that reason alone may be desirable from a patient's perspective. It also may assist in keeping this portion of the device from being pulled or otherwise disturbed by the patient and his surroundings while conducting everyday activities, and further may prevent or at least mitigate injury to the patient when the device is inadvertently bumped against external objects.

If desired, the access tube may also be formed from more than one material. For instance, the portion of the access tube that is to remain in a subcutaneous position may be made of a more rigid material, while the portion that is to remain in an extracorporeally accessible position may be made of a more flexible material. In such an embodiment, a cuff, as discussed in greater detail in U.S. application Ser. No. 10/351,172, which was previously incorporated by reference, could serve as the interface between the subcutaneous material and the percutaneous material. Or, to achieve a similar configuration, the subcutaneous portion could have a greater wall thickness than the portion that is to remain extracorporeally accessible.

For subcutaneous embodiments of the access tube apparatus, it may also be useful to use a flexible material to form the access tube. When made from a flexible material, such embodiments can be positioned as desired at safe, comfortable, and convenient locations that facilitate needle punctures of the skin and the use of access ports.

In the embodiment shown in FIG. 6A, the end of access tube 110 opposite from the anastomosis end 80 is configured to engage an access port 150. The access tube may be joined with the access port by any configuration suitable for engaging a portion of the access port 150. To achieve this, the access tube 110 may be configured to allow for a snap-fit, threaded, friction-fit or other suitable junction between it and the access port 150.

The access port 150 may optionally have suturing holes 153 for facilitating attachment of the port to the patient's tissue. These holes are but one example of structure that may facilitate securing the access port 150 and/or the access tube device itself to tissue.

As shown in FIG. 6A, the anastomosis end 80 of the access tube has an access tube anastomosis ring 85 adapted to cooperate with a target vessel anastomosis ring 40. Access tube anastomosis ring 85 is an example of a component of an anastomosis device that is attached to the access tube to facilitate anastomosis of the access tube to a target vessel. The access tube anastomosis ring 85 may also be configured to be integral with the access tube. Moreover, an anastomosis component other than an anastomosis ring may be used to facilitate anastomosis of the access tube to the target vessel. Any anastomosis component known to those of skill in the art that can be used to join vessels together with an access tube is within the scope of the present invention. The foregoing components and any others available to one of skill in the art are all examples of means for facilitating anastomosis of an access tube to a vessel. For example, the anastomosis component at the end of the access tube may be holes that have been preformed to facilitate suturing the access tube to a target vessel. Alternatively, as previously discussed, an anastomosis component need not be a part of the device at all. The access tube may simply be sutured directly to the target vessel wall, or be attached thereto by any other suitable method. An access tube that is soft enough to be punctured by suturing procedures, such as a graft vessel, is an example of an access tube with an anastomosis end adapted for attachment to the sidewall of a vessel that lacks an anastomosis component.

The target vessel anastomosis ring 40 preferably has posts 42 that are insertable into post slots 82, which are formed in access tube anastomosis ring 85. Preferably, the posts 42 fit inside the post slots 82 such that they are frictionally retained by the post slots 82. Accordingly, once the everted target vessel wall has been placed onto target vessel anastomosis ring 40, as discussed in greater detail later, the anastomosis end 80 of the access tube can be drawn closer to the anastomosis site and its position there can be frictionally maintained by driving the posts 42 further into the slots 82. Various other mechanisms can be used to hold the rings together, such as those disclosed in U.S. patent application Ser. No. 09/736,937 titled Locking Compression Plate Apparatus, which was filed on Dec. 14, 2000, the disclosure of which is expressly incorporated herein by reference. Target vessel anastomosis ring 40 is an example of a second means for facilitating anastomosis of an access tube to a vessel through cooperation with a first means for facilitating anastomosis. Of course, access tube anastomosis ring 85 may alternatively be the second means for facilitating anastomosis of an access tube to a vessel through cooperation with a first means for facilitating anastomosis, in which case target vessel anastomosis ring 40 may be the first means.

As indicated above, the access tube anastomosis ring 85 containing the slots 82 can be integrally formed with access tube 110 or it can be attached to access tube 110 by using any suitable attachment methodology, including any of various mechanical or medical bonding techniques. The access tube anastomosis ring 85 can be made of a variety of flexible, blood-compatible materials, such as polyurethane and the like. However, for reasons discussed below, access tube anastomosis ring 85 will typically be made of a less flexible material than that used to form the portion of access tube 110 defining the conduit 70.

Also, the target vessel anastomosis ring 40 preferably has holding tabs 46 extending towards the access tube or away from the target blood vessel. As discussed in greater detail later, the holding tabs 46 facilitate holding the perimeter of an opening in the target vessel wall in an everted position. Moreover, these holding tabs may be adapted to interdigitate to some degree with access tube holding tabs 86, which may be attached to or preferably integrally formed with the access tube anastomosis ring 85.

Figure 6B:
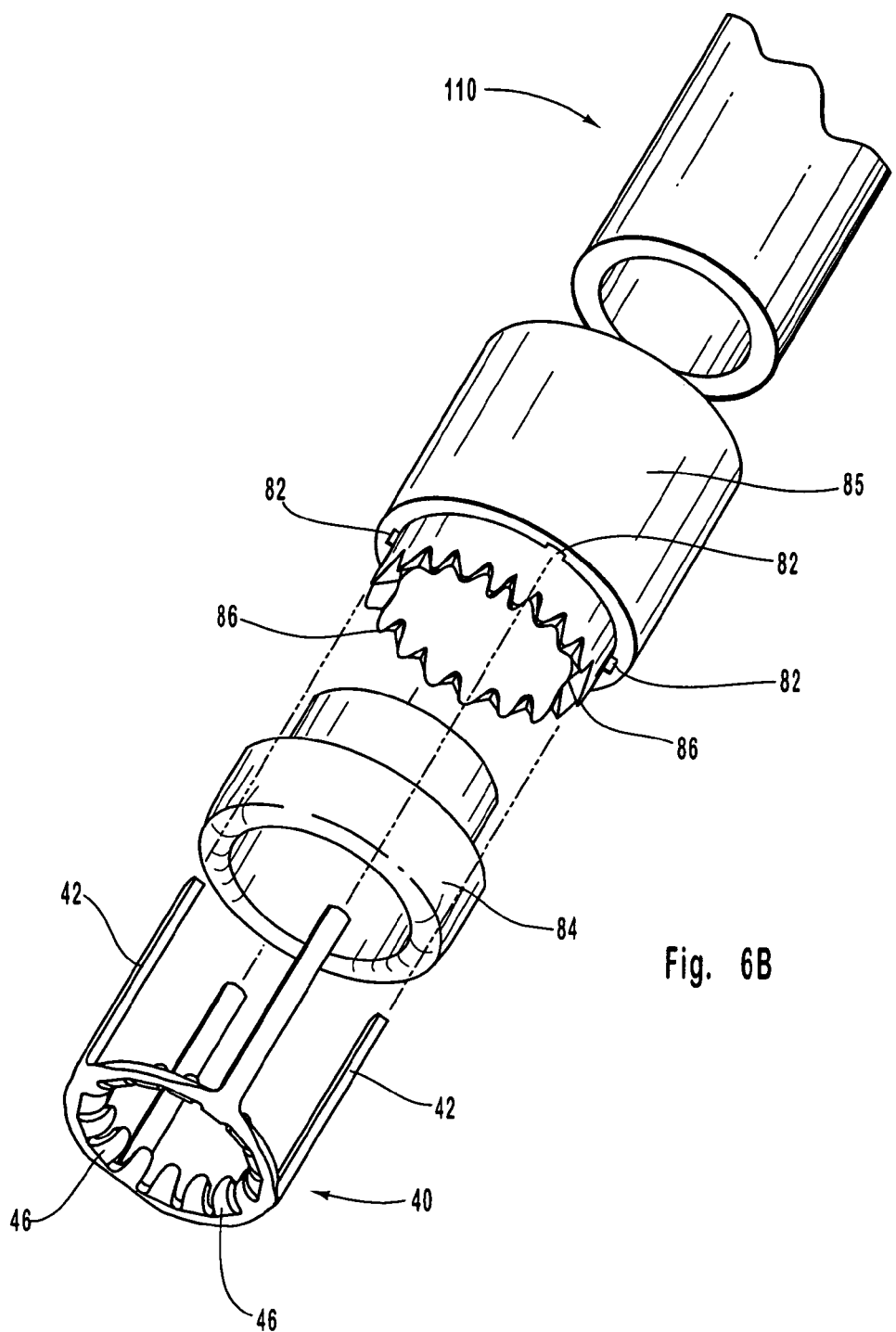
FIG. 6B is an enlarged, exploded perspective view of the anastomosis end of the device like that of FIG. 5A, but with the covering shown removed from the access tube anastomosis ring and exposing the access tube holding tabs.

Access tube holding tabs 86, along with a portion of the interior surface 72 of access tube conduit 70, may optionally be covered with a covering 84, as shown in FIG. 6A, and as shown separated from access tube holding tabs 86 in FIG. 6B. This covering is preferably made of a porous expanded polytetrafluoroethylene (ePTFE) or a material with similar properties, but could also be made from a variety of other materials. Still, any such material will typically be porous and allow for in-growth of biological tissue. In addition to providing a base for tissue in-growth, such a covering provides some cushion for forming a liquid-tight seal at the anastomosis site, and moreover allows the anvil apparatus (discussed later) to center itself more easily on access tube anastomosis ring 85.

In extracorporeally accessible embodiments of the present invention, as shown in FIG. 4, a portion of the access tube may be covered with a bio-compatible cuff 75. The cuff is typically placed on the access tube such that it is located just under the patient's skin. When so positioned, fibrous tissue can grow into the cuff such that it integrates with the patient's body and serves as a mechanical anchor to the access tube. The cuff could alternatively be placed at the skin layer. It also serves as a transcutaneous infection barrier. In one embodiment, the cuff is made from a polyester felt, but any suitable bio-compatible material could be used.

It should also be understood that various other embodiments within the scope of the present invention are possible. For instance, two separate access tubes need not be used. Instead, blood can be extracted from and inserted into the same access tube, either simultaneously in a dual-lumen access tube, or intermittently. In addition, only one access tube would be needed for other uses, such as withdrawing particularized amounts of blood for testing, inserting medications or other pharmacological agents into a patient's blood stream, etc.

Moreover, as previously discussed, the access tube of the present invention can comprise any of the various known or hereafter known tubular devices, such as graft vessels, catheters, etc. It should be apparent that many additional variations are possible, each of which remains within the scope of the invention.

As discussed above, the end of access tube 110 opposite from the anastomosis end 80 may have threads to engage with an access cap and/or access port 150. However, the access tube need not include threads. Any configuration designed to secure the access port 150 and/or access cap to the access tube is within the scope of the invention.

One method for anastomosing the access tube apparatus to the sidewall of a blood vessel is carried out by using an anvil apparatus, which includes an anvil 210 and an anvil pull 230, and an external anastomosis operator 700. Briefly stated, the anastomosis operator 700 functions to make an incision or access hole in the sidewall of a target vessel 10 at an anastomosis site and anastomose the access tube of the present invention to the target vessel at the access hole. The anvil apparatus, best seen in FIGS. 7A–7D, facilitates making the opening in the target vessel wall 10 through use with operator 700. The anvil apparatus may be intraluminally directed within the vessel to the anastomosis site or it may be externally positioned into the lumen at the anastomosis site.

More detailed information regarding methods for intraluminally directing an anvil apparatus is provided in U.S. patent application Ser. No. 09/736,839 titled "Intraluminally Directed Anvil Apparatus and Related Methods and Systems" and filed on Dec. 14, 2000, which is hereby expressly incorporated by reference. Also, more detailed information regarding methods for externally positioning an anvil apparatus is provided in U.S. patent application Ser. No. 10/003, 956, titled "Externally Positioned Anvil Apparatus for Cutting Anastomosis," which was filed on Oct. 31, 2001. U.S. patent application Ser. No. 10/003,956 is also hereby incorporated by reference.

As seen sequentially in FIGS. 7A–7F, a cutter 400 (discussed in greater detail later) engages anvil 210, thereby forming an opening in the target vessel wall. The anvil apparatus, used in connection with the operator 700, also facilitates everting the vessel tissue defining the opening over the holding tabs 46 of the target vessel anastomosis ring 40. The operator 700 then is used to draw the posts 42 of the target vessel anastomosis ring into the post slots 82 of the access tube anastomosis ring 85, which completes the anastomosis procedure. Of course, after the anastomosis procedure has been completed, the fluid occluder 90 is inserted into the access tube conduit 70 to maintain blood flow control at the anastomosis site.

Figure 7A:
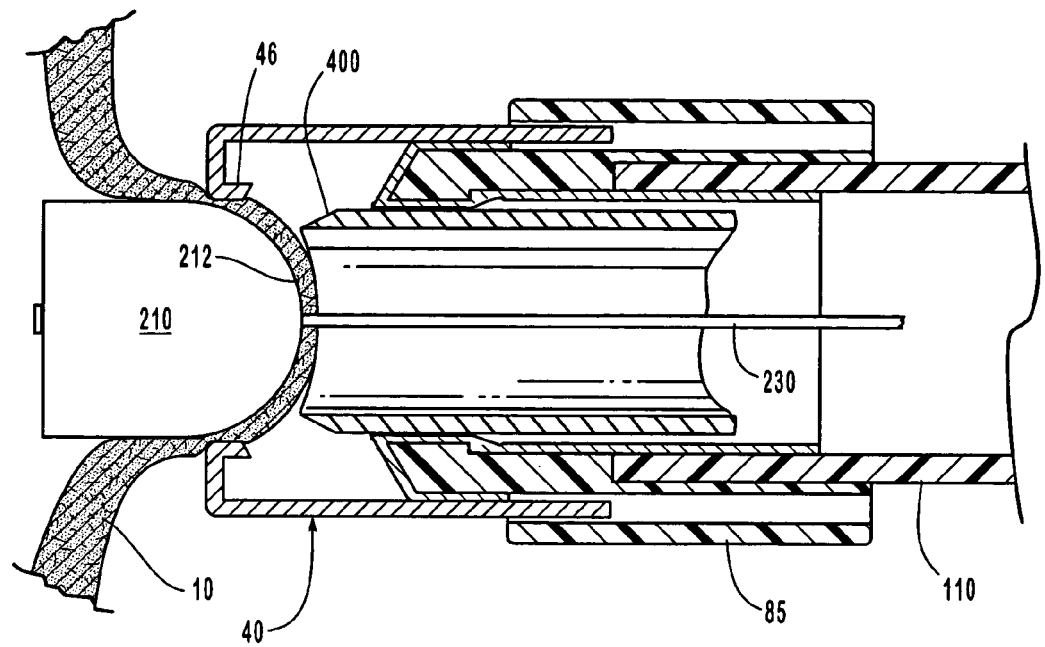
FIG. 7A is an enlarged cross-sectional view of the anvil apparatus distending the target vessel wall and the cutter of the external anastomosis operator being drawn towards the anvil apparatus.

FIG. 7A depicts anvil 210 being pulled into the target vessel anastomosis ring 40 and against the intima or interior wall of the target vessel 10. Also shown is cutter 400 extending through access tube 110 and approaching distended target vessel 10 on anvil 210.

Figure 7B:
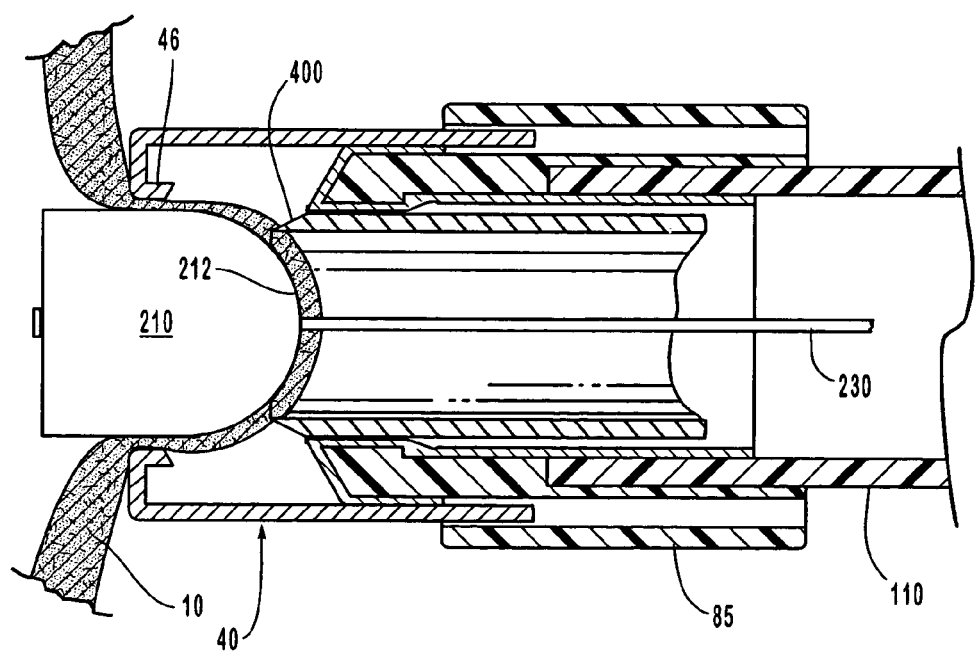
FIG. 7B is an enlarged cross-sectional view like that of FIG. 6A after the cutter has engaged the anvil apparatus to cut the target vessel wall and evert the target vessel tissue over the holding tabs.
Figure 7C:
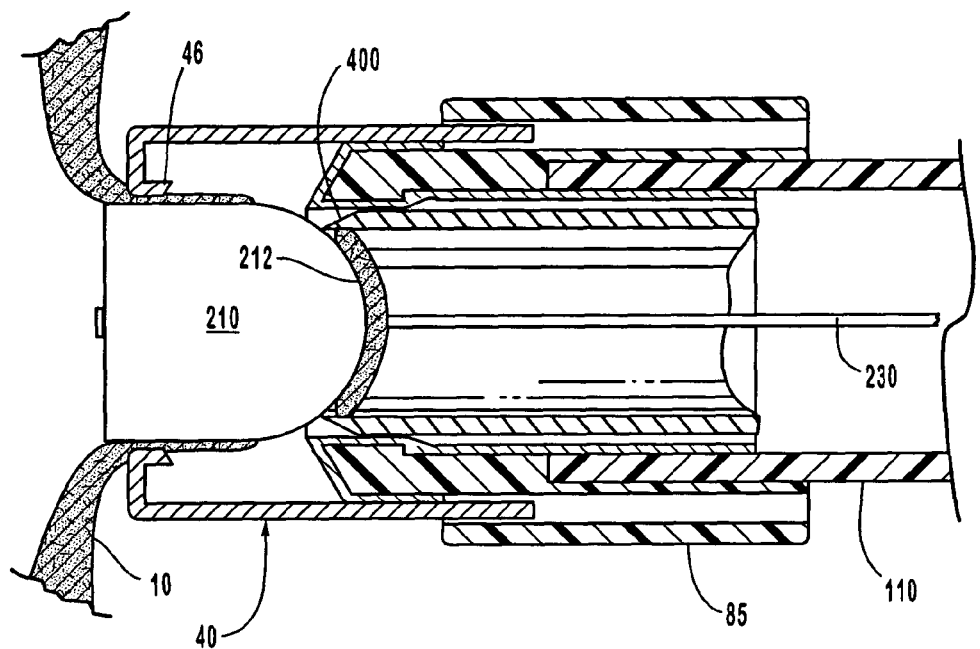
FIG. 7C is an enlarged cross-sectional view like that of FIG. 6B after the cutter has cut the target vessel wall, showing the target vessel tissue in a position to be everted over the holding tabs.

FIG. 7B depicts the formation of a target vessel opening in the wall of the target vessel 10. This opening is formed by pulling the anvil 210 towards cutter 400 such that cutter 400 engages the vessel wall. As shown in FIG. 7C, cutter 400 also engages anvil 210 so as to ensure a clean cut of the vessel wall. After the cut has been made, the portion of the target vessel wall that now defines the opening rests on the side or landing of anvil 210. This landing aids in everting the tissue that is to be anastomosed as a section of the tissue is held between the landing and holding tabs 46 with a length of tissue resting on the landing that is sufficient to be everted onto holding tabs 46.

Figure 7D:
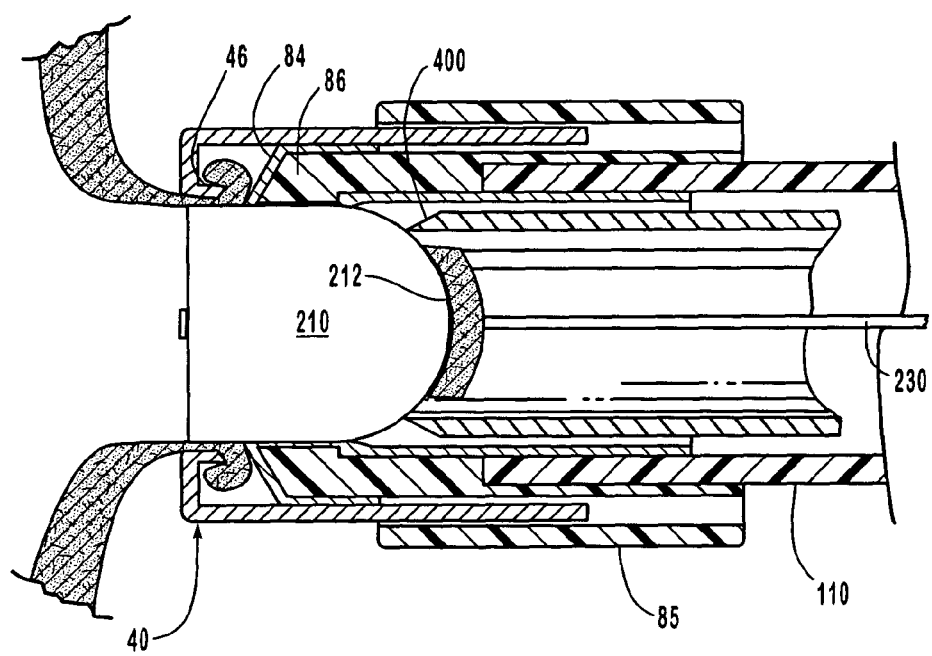
FIG. 7D is an enlarged cross-sectional view like that of FIG. 6C after the target vessel anastomosis ring has been drawn towards the access tube anastomosis ring to complete the anastomosis procedure.
Figure 7E:
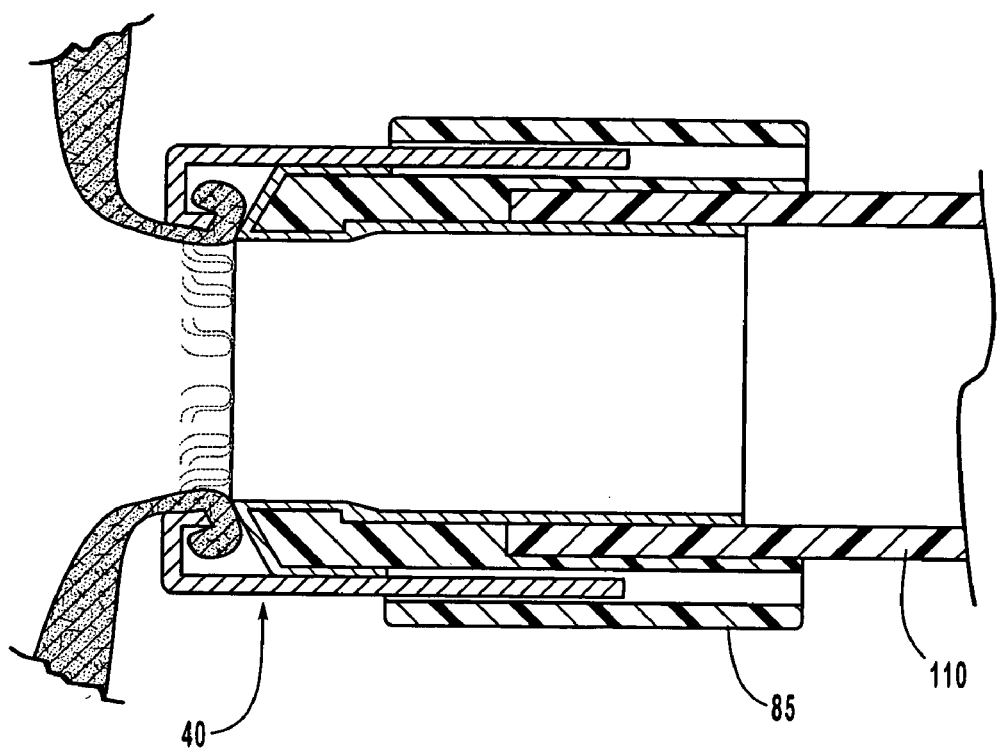
FIG. 7E is an enlarged cross-sectional view like that of FIG. 6D after the cutter and anvil apparatus have been withdrawn through the access tube conduit and the anastomosis procedure has been completed.
Figure 7F:
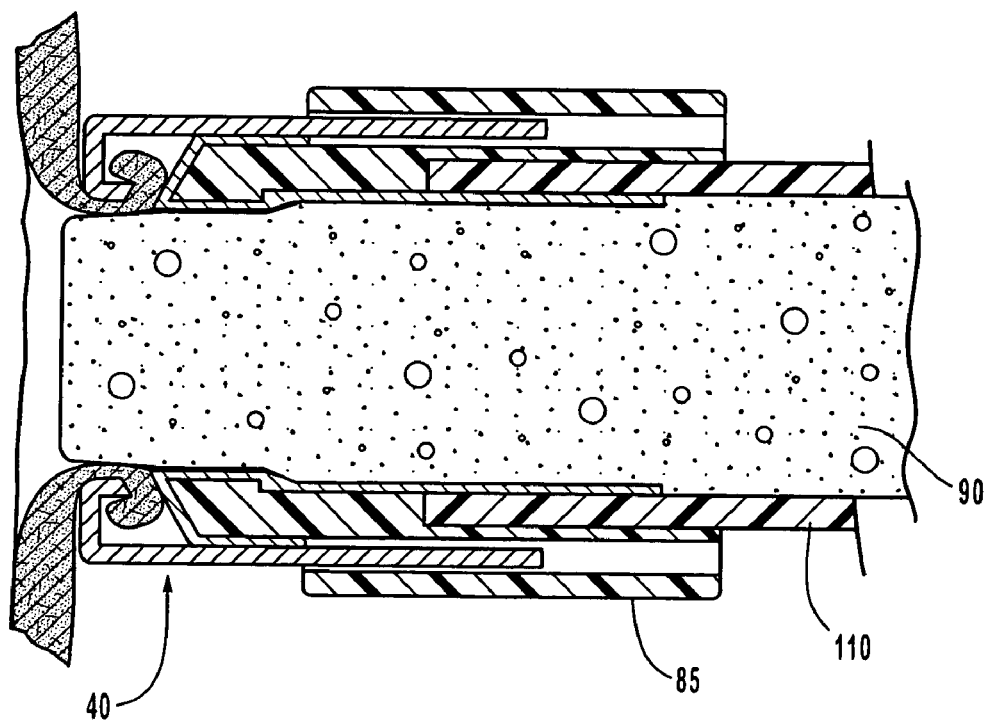
FIG. 7F is an enlarged cross-sectional view like that of FIG. 6E after the fluid occluder has been fully inserted inside the access tube.

As shown in FIG. 7D, access tube anastomosis ring 85 is then brought together with target vessel anastomosis ring 40. In doing so, holding tabs 46 with the everted tissue held thereon are approximated with holding tabs 86 on the access tube anastomosis ring 85. This will allow the tissue to contact the optional covering 84 on holding tabs 86. Note that holding tabs 46 and 86 may be circumferentially offset from each other such that the tabs are approximated with each other with tabs 46 directed towards spaces between tabs 86 in an interdigitated configuration. Once the anastomosis is completed, cutter 400 and anvil 210 are drawn through the access tube conduit 70 and out of access tube 110, such that conduit 70 is open as shown in FIG. 7E. Then, any of a variety of access ports will typically be attached to the access tube 110. Finally, as shown in FIG. 7F, the fluid occluder 90 is inserted into access tube conduit 70 to block fluid communication between the target vessel 10 and the conduit 70.

The external anastomosis operator 700, which is used to carry out the steps depicted in FIGS. 7A–7E, will now be described in greater detail. It should be understood, however, that although the following anastomosis method is disclosed in detail, many variations are possible, each of which remains within the scope of the present invention.

Figure 8A:
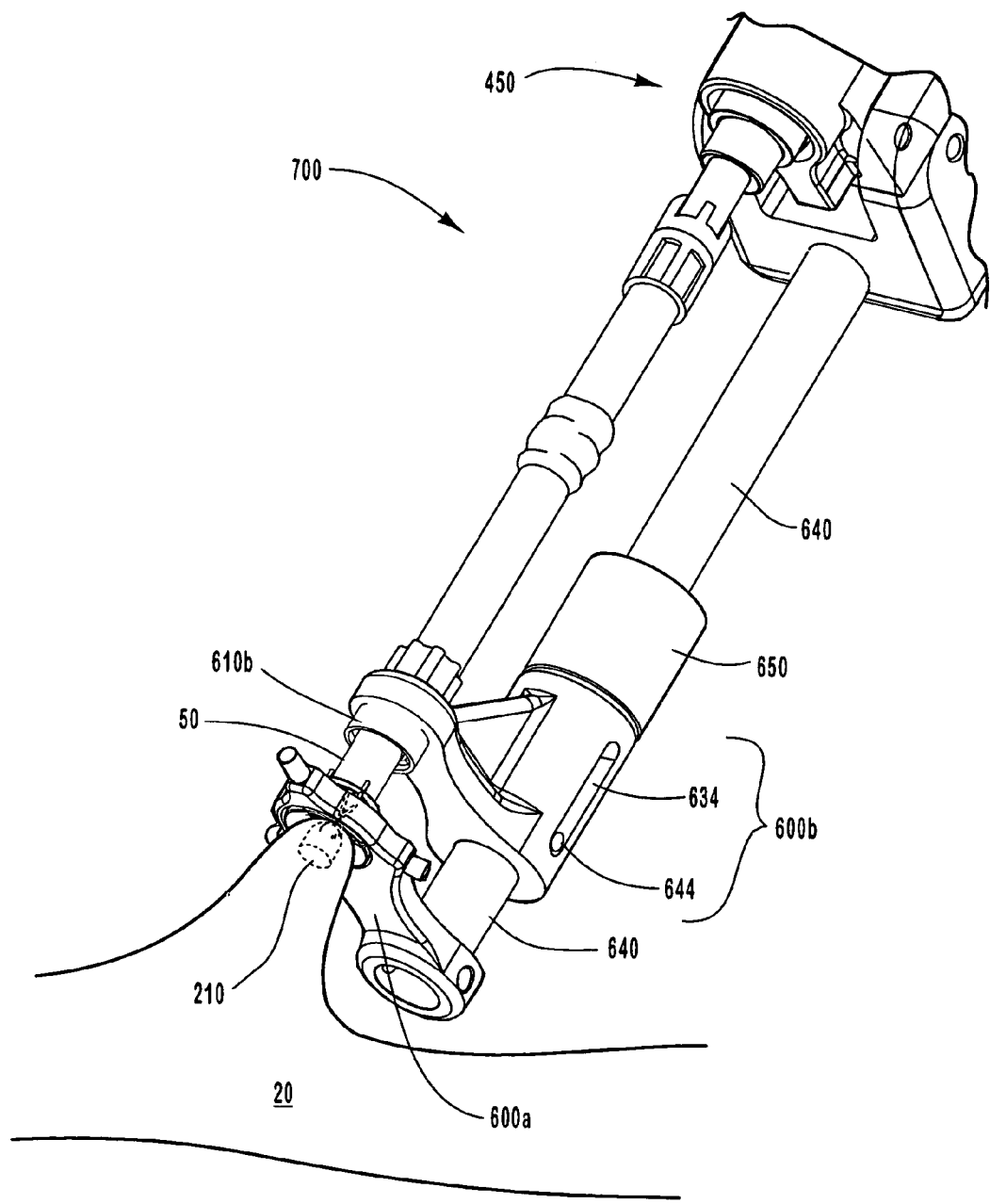
FIG. 8A is a perspective view of the external anastomosis operator engaging the anvil apparatus inside the target blood vessel during an anastomosis procedure.
Figure 8B:
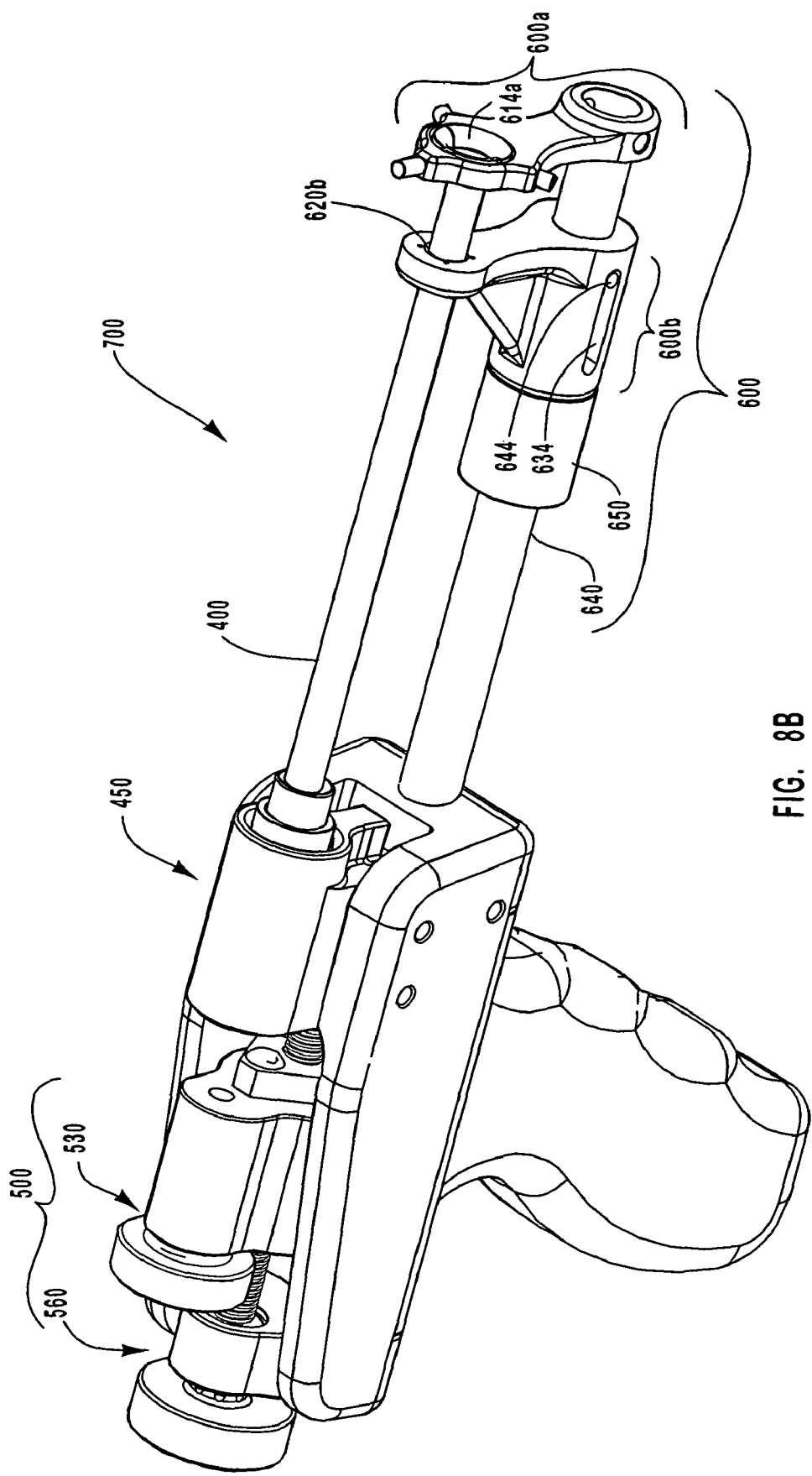
FIG. 8B is a perspective view of the external anastomosis operator.
Figure 8C:
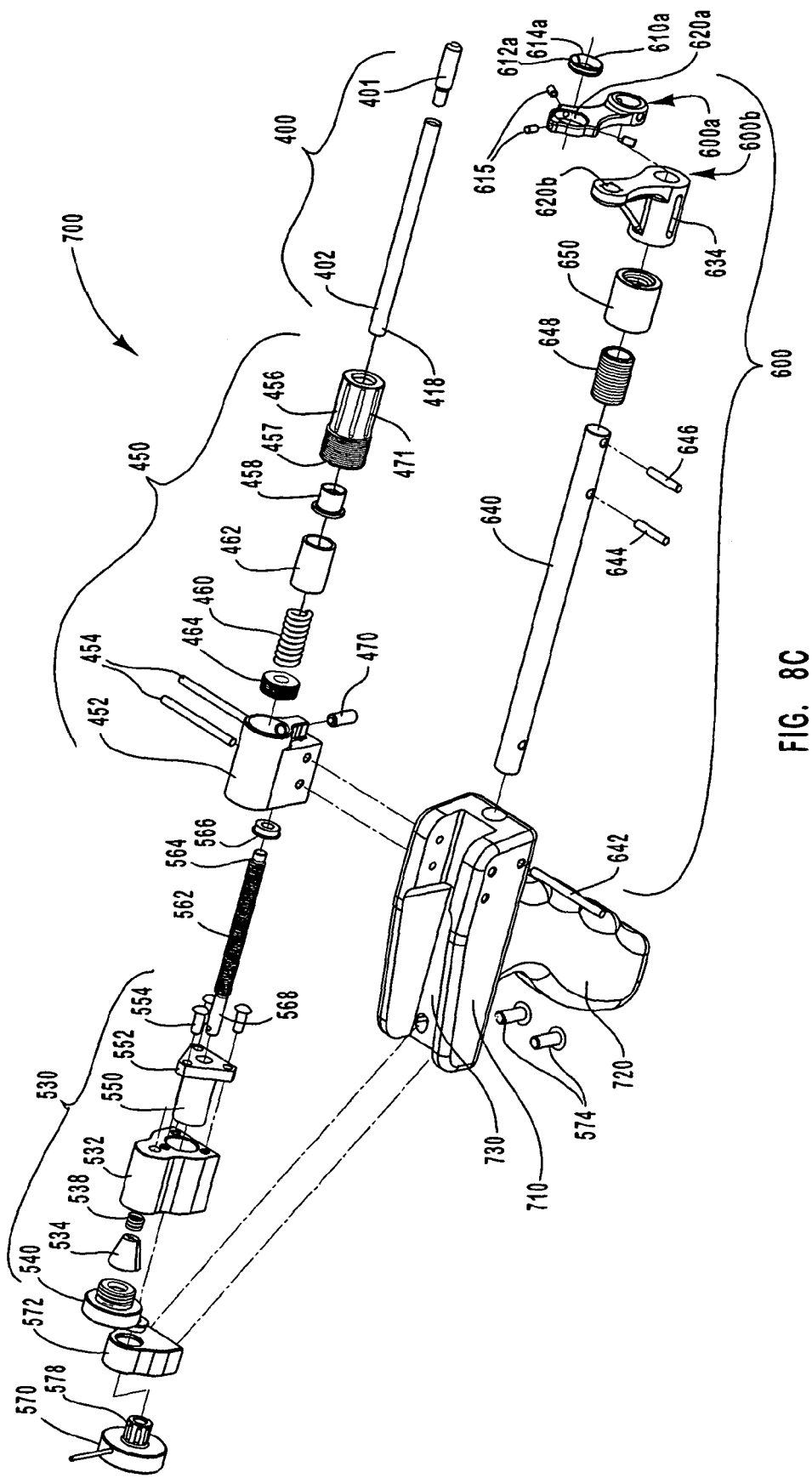
FIG. 8C is an exploded perspective view of the external anastomosis operator.

FIG. 8A shows the external anastomosis operator 700 with an attachment actuator 600 engaging an anvil in preparation for cutting an opening in the target vessel. As shown in FIGS. 8B–8D, external anastomosis operator 700 has a body 710 with an optional handle 720. Attached to body 710 are the main components of operator 700. These main components are cutter 400, spring biasing device 450, an anvil pull engager 500 which includes an anvil pull holder 530 and an anvil pull advancer 560, and an attachment actuator 600.

The attachment actuation devices and the attachment actuator 600 of external operator 700 may be adapted to enable the orientation of the target vessel anastomosis ring 40 and the access tube anastomosis ring 85 relative to each other to remain essentially the same as the rings are brought together to an anastomosis position. Note that once the opposing ring engagers of the attachment actuation devices or the attachment actuator 600 of external operator 700 have engaged the rings of an anastomosis device, preferably in a locked configuration, then the rings are easily brought together while maintaining their relative orientation. The opposing ring engagers may be guided together in a number of different ways. For example, attachment actuation device 600 may rely on guides to bring target vessel anastomosis ring engager 600a and access tube anastomosis ring engager 600b together. Alternatively, a hinge may be used to guide the opposing ring engagers 600a–b together. As discussed below in reference to attachment actuator 600, rail 640 guides the movement of one ring engager to the other. Mechanisms adapted to lock the ring engagers against the rings are also discussed below in reference to attachment actuator 600.

FIG. 8B provides a perspective view of an external anastomosis operator 700 with its main components identified including: cutter 400; spring biasing device 450, an anvil pull engager 500 which includes an anvil pull holder 530 and an anvil pull advancer 560, and an attachment actuation device 600. Spring biasing device 450 is used to apply pressure against the distal end 418 of cutter 400. One advantage derived from the use of a device such as the external anastomosis operator 700 is that such devices have a series of actuators, and by manipulating these actuators the operator can effectuate the different operations at the anastomosis site without actually having to manually and directly operate each element itself.

FIG. 8C provides an exploded perspective view of all of the components of external anastomosis operator 700 so it is with reference primarily to this view that the details of operator 700 are understood. FIGS. 8D–8E provide cross-sectional views of operator 700 depicting the steps for using operator 700.

Cutter 400 is shown in FIG. 8C as including a tip portion 401 and an extension portion 402. A spring biasing device 450 applies pressure against the distal end 418 of cutter 400. Spring biasing device 450 has a spring mount 452 that is mounted to body 710 via spring mount pins 454. A rotatable spring housing 456 is threadably engaged by spring mount 452. Loaded into rotatable spring housing 456 is a cutter cup 458 that is configured to hold distal end 418 of cutter. Cutter cup 458 has a flange that is pushed against a flange at the proximal end of rotatable spring housing 456 such that cutter cup 458 is held in the proximal end of spring housing 456. A spring 460 is positioned within a spring sleeve 462. Spring 460 and spring sleeve 462 have ends that abut cutter cup 458 and opposite ends that abut threaded jam screw 464. Threaded jam screw 464 is accessible via the distal end of spring mount 452 so that it may be rotated to increase or decrease the tension of spring 460 against cutter cup 458.

Cutter cup 458 moves within rotatable spring housing 456 against spring 460. The pressure of spring 460 against cutter cup 458 enables cutter 400 to apply pressure against anvil 210 as anvil 210 is pulled against cutter 400. This makes it easier to cut the vessels as force is being applied in both directions. It also enables cutter 400 to be pushed back by anvil 210 to allow anvil 210 to further distend the wall of vessel 10 as shown in FIGS. 7A–7C until sufficient pressure is applied by spring 460 to bias cutter 400 forward and by the advancement of anvil 210 by anvil pull 230 to cut the vessel. The gradual increase in pressure also serves to assist a spherical engaging end 212 of anvil 210 to self center on cutter 400. More particularly, anvil 210 may be initially misaligned such that the center of engaging end from which anvil pull extends is positioned on the cutting edge of the cutter. A rapid application of pressure would lock such a misalignment while a gradual increase enables the curvature of spherical engaging end to guide the anvil into a centered orientation.

Another function of spring biasing device 450 is to set the position of cutter 400. Rotatable spring housing 456 has a notch 457 at its distal end that enables a screw driver to rotate rotatable spring housing 456 within spring mount 452 to advance or retract rotatable spring housing 456 within spring mount 452. Movement of rotatable spring housing 456 also moves cutter cup 458, thereby determining the location of distal end 418 of cutter 400 within operator 700. Of course, advancement of cutter cup 458 towards the proximal end of operator 700 causes cutting knife 400 to engage anvil 210 closer to target vessel anastomosis ring 40 while retraction of cutter cup 458 towards the distal end of operator 700 causes cutting knife 400 and anvil 210 to engage each other closer to access tube anastomosis ring 85. The position of cutter 400 is preferably set to enable vessel 10 to be distended in a manner that is optimal for then subsequently everting the portion defining the newly formed opening onto holding tabs 46. To carefully identify the length that rotatable spring housing 456 is advanced or retracted, a detent 470 is threaded into spring mount such that it can contact rotatable spring housing and engage the grooves 471 of rotatable spring housing in a manner that enables detent 470 to click as each groove is rotated past detent 470.

Obviously spring biasing device 450 has many variables that impact the manner in which cutter 400 is used in combination with external anastomosis operator 700. Some of these variables include the inherent tension of spring 460, the tension of spring 460 as caused by the position of threaded jam screw 464 in spring mount 452 against spring 460, and the position of the surface which distal end 418 of cutter 400 abuts, namely cutter cup 660 as determined by the position of rotatable spring housing 456 within spring mount 452.

Spring biasing device 450 is an example of spring biasing means for providing tension against the cutting means as the cutting means engages the anvil means of the intraluminally directed anvil apparatus. The spring biasing means provides an amount of tension that enables the cutting means to form the vessel opening after the wall of the target vessel has been distended by the action of the anvil means being pulled into the openings of the ring assembly such that forming the target vessel opening results in at least partial eversion of the portion of the first vessel defining the first vessel opening.

As indicated above, anvil pull engager 500 has two primary components including an anvil pull holder 530 and anvil pull advancer. Anvil pull holder 530 receives anvil pull 230 via spring biasing device 450. More particularly, anvil pull 230 extends through cutter cup 458, rotatable spring housing 456, spring 460 and sleeve 462 around spring 460, and out of threaded jam screw 464.

Anvil pull holder 530 includes a holder mount 532 positioned in track 730 of body 710. In this embodiment, the holder mount is moveable so that the anvil pull can be advanced after it is held. However, in other embodiments, the anvil pull holder may just lock the anvil pull into position such that the cutter is moved against a stationary anvil. Similarly, the spring biasing device 450 may be eliminated so that the vessel is cut only by pressure exerted by the anvil pull against the cutter. As discussed above, while the cutter and the anvil may engage each other in these arrangements, it is preferable for the cutter to apply some pressure as the anvil pull is advanced against the cutter.

Holder mount 532 may be utilized in different ways to hold anvil pull 230. Holder 530 has a split cone 534 inserted into a tapered chamber (not shown) against a spring 538. Anvil pull 230 extends through apertures in holder mount 532, spring 538, split cone 534 and out of an aperture centered in holder knob 540. Holder knob 540 is threadably engaged by holder mount 532 such that rotation of holder knob 540 advances split cone 534 in the tapered chamber, causing split cone to lock onto anvil pull 230. Holder mount is slotted at its distal end as is holder knob. By aligning a slot (not shown) in holder knob 540 with an insert slot (not shown) in the holder mount, anvil pull 230 can be bent so that it extends through both the holder knob slot and the insert slot. Then holder knob 540 can then be rotated so that the bent portion of anvil pull 230 is rotated into one of the locking slots that extend perpendicularly from the insert slot. This securely locks anvil pull into position. Anvil pull 230 can be locked through the use of slots instead of or in addition to the use of split cone 534 in the tapered chamber.

Since anvil pull holder 530 is moveable it threadably engages rotatable lead screw 562 of anvil pull advancer. More particularly, lead screw 562 is threadably engaged by anti-backlash nut 550 which is fixedly attached to holder mount 532. Anti-backlash nut 550 has an attachment face 552 through which a plurality of attachment face screws 554 extend to hold holder mount 532 and anti-backlash nut 550 together.

Lead screw 562 has a proximal pivot end 564 that rotates within a bushing 566 positioned within a recess in spring mount 452. Lead screw also has a distal pivot end 568 that is attached to advancer knob 570 to rotate lead screw 562. Advancer knob 570 rotates within an advancer knob mount 572 which is attached to body 710 in groove 730 via advancer knob mount bolts 574. As shown in FIG. 8D, distal pivot end 568 rotates in a bushing 576 positioned within an aperture of advancer knob mount 572.

Advancer knob 570 has a stem with a plurality of grooves 578 that engage a detent (not shown) to click so that the incremental rotation of advancer knob 570 can be carefully counted to determine the length that the anvil is moved in the anastomosis device as the anvil pull is advanced. The detent is threaded into advancer knob mount 572 such that it can contact grooves 578 in the stem of advancer knob 570 to click as each groove is rotated past the detent.

FIGS. 8D–8E depict advancer knob 570 being rotated to move anvil pull advancer 560 so that it can urge anvil pull 230 in a manner such that anvil 210 is advanced within target vessel anastomosis ring 40. As advancer knob 570 is rotated, lead screw 562 is thereby rotated. Since anvil pull holder 530 is threadably engaged on rotatable lead screw 562 and is locked in track 730, anvil pull holder 530 can only move forward and backward as lead screw 562 is rotated.

FIG. 8E depicts attachment actuation device 600 prior to being engaged. Attachment actuation device 600 has a target vessel anastomosis ring engager 600a and a second access tube anastomosis ring engager 600b. Target vessel anastomosis ring engager 600a and anastomosis ring engager 600b each respectively utilize an optional adaptor 610a–b to engage the target vessel anastomosis ring 40 and access tube anastomosis ring 85, as shown in FIG. 8C. Target vessel anastomosis ring engager 600a and access tube anastomosis ring engager 600b each have a cutter aperture 620a and 620b (shown in FIG. 8C). Cutter 400 extends through these aligned apertures 620a–b. As shown in FIG. 8D, target vessel anastomosis ring engager 600a is positioned on rail 640 such that it extends slightly beyond cutting edge 414 of cutter 400. This difference in length enables target vessel anastomosis ring 40 to be held in a manner that permits the wall of the target vessel to be pulled into anastomosis device as shown in FIGS. 7A–7D and distended as needed.

Rail 640 is attached to body 710 (identified in FIG. 8C) via rail pin 642. A groove pin 644 extends through rail 640. An anastomosis ring holder pin 646 holds the target vessel anastomosis ring engager 600a on the proximal end of rail 640.

Target vessel anastomosis ring engager 600a is fixedly mounted on rail 640 via pin 646 while access tube anastomosis ring engager 600b is movably mounted on rail 640. Access tube anastomosis ring engager 600b has a groove 634 through which groove pin 644 extends. The configuration of groove pin 644 in groove 634 enables access tube anastomosis ring engager 600b to be held in a fixed orientation such that it can be moved back and forth as needed with respect to target vessel anastomosis ring engager 600a.

Access tube anastomosis ring engager is moved on rail 640 by rotating threaded compressor sleeve 650 which engages a threaded rail sleeve 648. Threaded rail sleeve 648 may be adhered onto rail 640 or be an integral component. Rail 640 and its threaded rail sleeve 648 or threaded rail portion combined with compressor sleeve 650 are means for advancing one ring engager towards the other ring engager.

Set screws 615 lock target vessel anastomosis ring engager 600a on target vessel anastomosis ring 40. Access tube anastomosis ring engager 600b may have a latch (not shown) that enables engager 600b to lock onto access tube anastomosis ring 85. Once the anastomosis is complete, set screws 615 and the latch are released to release the anastomosis and access tube anastomosis ring engagers from the rings. Note that there are many other ways for locking the rings with anastomosis and access tube anastomosis ring engagers 600a–b such as the use of conventional quick release configurations. Quick release configurations, latches and set screws are all examples of means for locking the ring engagers against the rings.

The anastomosis device is preferably used for vascular anastomosis, however, the present invention is not limited to such use. Nor is the anastomosis device limited to use with any particularly sized vessel or access tube. For example, vessels and access tubes may be anastomosed with diameters ranging from about 2 mm to about 20 mm, but there is no fundamental limitation for using embodiments of this invention with vessels or access tubes with diameters in this range.

It will be obvious to those having skill in the art that many changes may be made to the details of the above-described embodiments of this invention without departing from the underlying principles thereof. The scope of the present invention should, therefore, be determined only by the following claims.

The invention claimed is:

1. A method for repeatedly accessing a body fluid such as blood in an anatomical vessel, comprising:
    obtaining an access tube having an access end and an anastomosis end with a conduit extending from the access end to the anastomosis end;
    anastomosing the anastomosis end of the access tube to a side of an anatomical vessel;
    occluding the conduit of the access tube with a fluid in direct contact with the access tube to act as a fluid occluder which is exposed to the body fluid,
    wherein the conduit has a perimeter which enables the surface tension of the fluid occluder to prevent intermixing of the fluid occluder and the body fluid along the entire length of the conduit until occlusion is no longer needed;
    wherein the fluid occluder has at least one properly, which in cooperation with the perimeter of the conduit, enables a sufficient amount of the fluid occluder to remain in the conduit such that the body fluid is prevented from extending into the entire length of the conduit until occlusion is no longer needed; and
    removing the fluid occluder from the access tube to provide fluid communication between the lumen of the vessel and the conduit of the access tube.

2. The method of claim 1, wherein the access tube is anastomosed at the anastomosis opening without extending significantly into the lumen of the vessel.

3. The method of claim 1, wherein the step of removing the fluid occluder is done by penetrating a self-sealing port connected to the access tube.

4. The method of claim 1, wherein the fluid occluder comprises a highly viscous fluid.

5. The method of claim 1, wherein the fluid occluder is a gel.

6. The method of claim 1, wherein the fluid occluder comprises a fluid of low viscosity.

7. The method of claim 1, wherein the fluid occluder is a saline solution.

8. The method of claim 1, wherein the fluid occluder has a pharmacological substance incorporated therein.

9. The method of claim 1, wherein the step of anastomosing is done by suturing.

10. The method of claim 1, further comprising the step of reoccluding the conduit with a fluid occluder to prevent flow through the conduit.

11. The method of claim 1, wherein the body fluid is blood.

12. The method of claim 11, further comprising the step of providing fluid communication between the conduit of the access tube and a blood treatment device.

13. The method of claim 12, further comprising the step of providing fluid communication between the blood treatment device and a second access tube anastomosed to a second vessel to re-introduce the treated brood.

14. The method of claim 12, further comprising the step of providing fluid communication between the blood treatment device and a second access tube anastomosed to the vessel at another location to re-introduce the treated blood.

15. The method of claim 12, further comprising the step of re-introducing the treated blood back through the access tube conduit.

16. The method of claim 1, wherein the anastomosed access tube extends percutaneously with the access end being extracorporeally positioned.

17. The method of claim 1, wherein the entire access tube is positioned subcutaneously after anastomosis to the vessel has been completed.

18. The method of claim 1, wherein the access tube is closed at the access end.

19. The method of claim 18, wherein the access tube is closed at the access end with an access cap.

20. The method of claim 1, wherein the fluid occluder isolates any non-native materials from contact with the body fluid until access is desired and the fluid occluder is removed.

21. A system for facilitating repeated percutaneous access to a body fluid such as blood in an anatomical vessel, comprising:
    a fluid occluder;
    an access tube having an access end and an anastomosis end with a conduit extending from the access end to the anastomosis end, wherein the anastomosis end is configured to be attached to a side of an anatomical vessel; and
    a port coupled to the access tube, wherein the port is configured to allow the fluid occluder to be inserted into the access tube such that the fluid occluder is not contained in another structure, such that said fluid occluder is in direct contact with the access tube, and such that the access tube becomes occluded at its anastomosis end after a sufficient volume of fluid occluder has been inserted into the access tube to contact the body fluid; wherein the fluid occluder has at least one property which in cooperation with the perimeter of the conduit enables a sufficient amount of the fluid occluder to remain in the conduit such that the body fluid is prevented from extending into the entire length of the conduit until occlusion is no longer needed.

22. The system of claim 21, wherein the fluid occluder comprises a highly viscous fluid.

23. The system of claim 21, wherein the fluid occluder is a gel.

24. The system of claim 21, wherein the fluid occluder comprises a fluid of low viscosity.

25. The system of claim 21, wherein the fluid occluder is a saline solution.

26. The system of claim 21, wherein the port is a self-sealing port.

27. The system of claim 21, wherein the access tube is configured to be attached to the vessel at an anastomosis opening without extending significantly into the vessel lumen.

28. The system of claim 21, further comprising a component of an anastomosis device at the anastomosis end of the access tube.

29. The system of claim 28, wherein the component is an anastomosis ring.

30. The system of claim 21, wherein the access tube is closed at the access end.

31. A system for facilitating repeated percutaneous access to a body fluid such as blood in an anatomical vessel, comprising:
    access tube means for accessing an anastomosed vessel, wherein the access tube means has an access end opposite from an anastomosis end with a conduit extending from the access end to the anastomosis end;
    fluid occluding means for occluding the access tube means; and
    port means for accessing the access tube means, wherein the port means is configured to allow the fluid occluding means to be inserted into the access tube means such that the fluid occluding means is in direct contact with the access tube means and the access tube means becomes occluded at its anastomosis end after a sufficient volume of fluid occluding means has been inserted into the access tube means to contact the body fluid; wherein the fluid occluding means has at least one property, which in cooperation with the perimeter of the conduit, enables a sufficient amount of the fluid occluding means to remain in the conduit such that the body fluid is prevented from extending into the entire length of the conduit until occlusion is no longer needed.

32. The system of claim 31, wherein the fluid occluding means has a pharmacological agent incorporated therein.

33. The system of claim 31, wherein the access tube means further comprises first means for facilitating anastomosis of the access tube means to the vessel.

34. The system of claim 33, wherein the access tube means further comprises second means for facilitating anastomosis of the access tube means to the vessel through cooperation with the first means for facilitating anastomosis of the access tube means to the vessel.

35. The system of claim 31, wherein the fluid occluding means comprises a highly viscous fluid.

36. The system of claim 31, wherein the fluid occluding means is a gel.

37. The system of claim 31, wherein the fluid occluding means comprises a fluid of low viscosity.

38. The system of claim 31, wherein the fluid occluding means is a saline solution.

39. The system of claim 31, wherein the port means is self-sealing.

40. The system of claim 31, wherein the access tube means is configured to be attached to the vessel at an anastomosis opening without extending significantly into the vessel lumen.

41. The system of claim 31, wherein the access tube means is closed at the access end.

* * * * *

UNITED STATES PATENT AND TRADEMARK OFFICE
CERTIFICATE OF CORRECTION

PATENT NO. : 7,124,570 B2 Page 1 of 1
APPLICATION NO. : 10/624711
DATED : October 24, 2006
INVENTOR(S) : Blatter et al.

It is certified that error appears in the above-identified patent and that said Letters Patent is hereby corrected as shown below:

On the Title Page, Item (57)

In the "Abstract," at line 5, it reads ". . . with an fluid . . .", which should read --with a fluid--

Column 18, Line 18 reads, ". . . the treated brood." which should read --. . . the treated blood.--

Signed and Sealed this

Thirtieth Day of September, 2008

JON W. DUDAS
*Director of the United States Patent and Trademark Office*